United States Patent
Kishi et al.

(10) Patent No.: US 12,217,535 B2
(45) Date of Patent: Feb. 4, 2025

(54) BIOLOGICAL INFORMATION ACQUISITION DEVICE AND BIOLOGICAL INFORMATION ACQUISITION METHOD

(71) Applicant: Mitsubishi Electric Corporation, Tokyo (JP)

(72) Inventors: Chihiro Kishi, Tokyo (JP); Hirotaka Sakamoto, Tokyo (JP); Atsushi Matsumoto, Tokyo (JP); Shintaro Watanabe, Tokyo (JP); Jun Ishii, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 360 days.

(21) Appl. No.: 17/799,797

(22) PCT Filed: Apr. 6, 2020

(86) PCT No.: PCT/JP2020/015517
§ 371 (c)(1),
(2) Date: Aug. 15, 2022

(87) PCT Pub. No.: WO2021/205508
PCT Pub. Date: Oct. 14, 2021

(65) Prior Publication Data
US 2023/0089508 A1    Mar. 23, 2023

(51) Int. Cl.
*G06V 40/10*    (2022.01)
*G06T 7/00*    (2017.01)
(Continued)

(52) U.S. Cl.
CPC ............ *G06V 40/15* (2022.01); *G06T 7/0012* (2013.01); *G06V 20/597* (2022.01); *G06V 40/178* (2022.01); *G06T 2207/30196* (2013.01)

(58) Field of Classification Search
CPC .... G06V 40/15; G06V 20/597; G06V 40/178; G06T 7/0012; G06T 2207/30196
(Continued)

(56) References Cited

U.S. PATENT DOCUMENTS 10,509,975 B2 * 12/2019 Bieg .................. G06F 3/012
2013/0071875 A1 * 3/2013 Zemer ................ G01N 15/1433
382/128

(Continued)

FOREIGN PATENT DOCUMENTS

JP    2016-077890 A    5/2016
JP    2017-124058 A    7/2017
(Continued)

OTHER PUBLICATIONS

International Search Report for PCT/JP2020/015517 dated Jun. 23, 2020.

*Primary Examiner* — William D Titcomb
(74) *Attorney, Agent, or Firm* — Sughrue Mion, PLLC

(57) ABSTRACT

A biological information acquisition device includes a detection-value acquisition unit to acquire a detection value from a non-contact biometric sensor, a vital measurement unit to measure a vital sign of a target person (TP) using the detection value, an image-data acquisition unit to acquire image data indicating an image captured by a camera, an image processing unit to perform at least one of a state estimation process of estimating a state of the target person, an attribute estimation process of estimating an attribute of the target person, or a personal identification process of identifying the target person by performing image processing on the image captured including the target person, and a parameter setting unit to set a parameter in measuring the vital sign in accordance with a result of the image processing.

19 Claims, 12 Drawing Sheets

(51) Int. Cl.
*G06V 20/59* (2022.01)
*G06V 40/16* (2022.01)

(58) Field of Classification Search
USPC .......................................................... 382/128
See application file for complete search history.

(56) References Cited

U.S. PATENT DOCUMENTS

| | | | |
|---|---|---|---|
| 2015/0367780 A1* | 12/2015 | Hilsebecher | A61B 3/113 |
| | | | 348/78 |
| 2016/0100766 A1* | 4/2016 | Yoshioka | A61B 5/0082 |
| | | | 600/301 |
| 2019/0073510 A1* | 3/2019 | West | G06F 18/40 |
| 2019/0279447 A1* | 9/2019 | Ricci | B60N 2/0022 |
| 2020/0020226 A1* | 1/2020 | Stenneth | G06V 20/597 |
| 2020/0081611 A1* | 3/2020 | Beaurepaire | G06F 9/451 |
| 2020/0163609 A1* | 5/2020 | Lisi | A61B 5/055 |
| 2023/0089508 A1* | 3/2023 | Kishi | G16H 30/40 |
| | | | 382/128 |

FOREIGN PATENT DOCUMENTS

| | | |
|---|---|---|
| JP | 2018-117740 A | 8/2018 |
| JP | 2019-170967 A | 10/2019 |

* cited by examiner

FIG. 5

|  | | Parameter | | | |
|---|---|---|---|---|---|
|  | | First Parameter (Irradiation Position) | Fourth Parameter (Measurement Range) | Second Parameter (Frame) | Third Parameter (Section Width) |
| State | Heart Position | ● | | | |
| | Amount of Body Motion | | | ● | ● |
| | Degree of Mouth Opening | | | ● | ● |
| | Expression Value | | ● | | |
| Attribute | Age | | ● | | |
| | Gender | | ● | | |
| Personal Identification Information | | ● | ● | | |

BIOLOGICAL INFORMATION ACQUISITION DEVICE AND BIOLOGICAL INFORMATION ACQUISITION METHOD

CROSS REFERENCE TO RELATED APPLICATIONS

This application is a National Stage of International Application No. PCT/JP2020/015517 filed Apr. 6, 2020.

TECHNICAL FIELD

The present disclosure relates to a biological information acquisition device and a biological information acquisition method.

BACKGROUND ART

Conventionally, a radio-wave non-contact biometric sensor for in-vehicle use has been developed. Patent Literature 1 discloses a technique of measuring the heart rate of a driver using such a non-contact biometric sensor.

CITATION LIST

Patent Literatures

Patent Literature JP 2017-124058 A

SUMMARY OF INVENTION

Technical Problem

Patent Literature 1 discloses a technique of estimating the position of the heart of a driver on the basis of the position of a driver's seat in a vehicle. In addition, Patent Literature 1 discloses a technique of adjusting the directivity of a non-contact biometric sensor depending on the estimated position (See, for example, paragraph [0015] in Patent Literature 1). As a result, it is expected to accurately measure a heart rate regardless of the position of the driver's seat in the vehicle.

However, the parameter to be adjusted for improving the measurement accuracy is not limited to the directivity of the non-contact biometric sensor. From the viewpoint of improving the measurement accuracy, it is preferable to adjust various parameters. In the adjustment based on the position of the drivers seat in the vehicle, there is a problem that it is difficult to achieve the adjustment of such various parameters.

The present disclosure has been made to solve the above problems, and an object of the present disclosure is to provide a biological information acquisition device and a biological information acquisition method that enable the adjustment of various parameters in measurement using a non-contact biometric sensor.

Solution to Problem

A biological information acquisition device according to the present disclosure includes processing circuitry configured to acquire a detection value from a non-contact biometric sensor; measure a vital sign of a target person using the detection value; acquire image data indicating an image captured by a camera; perform at least one of a state estimation process of estimating a state of the target person, an attribute estimation process of estimating an attribute of the target person, or a personal identification process of identifying the target person by performing image processing on the image captured including the target person; and set a parameter in measuring the vital sign in accordance with a result of the image processing, wherein the parameter includes a fourth parameter corresponding to a measurement range of the vital sign in the measurement, the processing circuitry sets the fourth parameter in accordance with at least one of a result of the state estimation process, a result of the attribute estimation process, or a result of the personal identification process, the state estimation process includes a process of estimating an expression of the target person, the attribute estimation process includes at least one of a process of estimating an age of the target person or a process of estimating a gender of the target person, personal identification information corresponding to the target person is acquired by performing the personal identification process, and the processing circuitry sets the fourth parameter in accordance with at least one of the expression, the age, the gender, or the personal identification information.

A biological information acquisition method according to the present disclosure includes acquiring a detection value from a non-contact biometric sensor; measuring a vital sign of a target person using the detection value; acquiring image data indicating an image captured by a camera; performing at least one of a state estimation process of estimating a state of the target person, an attribute estimation process of estimating an attribute of the target person, or a personal identification process of identifying the target person by performing image processing on the image captured including the target person; and setting a parameter in measuring the vital sign in accordance with a result of the image processing, wherein the parameter includes a fourth parameter corresponding to a measurement range of the vital sign in the measurement, and the method further comprises setting the fourth parameter in accordance with at least one of a result of the state estimation process, a result of the attribute estimation process, or a result of the personal identification process, and wherein the state estimation process includes a process of estimating an expression of the target person, the attribute estimation process includes at least one of a process of estimating an age of the target person or a process of estimating a gender of the target person, personal identification information corresponding to the target person is acquired by performing the personal identification process, and the method comprises setting the fourth parameter in accordance with at least one of the expression, the age, the gender, or the personal identification information.

Advantageous Effects of Invention

According to the present disclosure, with the configuration described above, it is possible to provide a biological information acquisition device and a biological information acquisition method that enable the adjustment of various parameters in measurement using a non-contact biometric sensor.

BRIEF DESCRIPTION OF DRAWINGS

FIG. 5 is an explanatory diagram illustrating a correspondence relationship between information output by the image processing unit and parameters set by the parameter setting unit.

DESCRIPTION OF EMBODIMENTS

Hereinafter, in order to describe the present disclosure in more detail, modes for carrying out the present disclosure will be described with reference to the accompanying drawings.

First Embodiment

Figure 1:
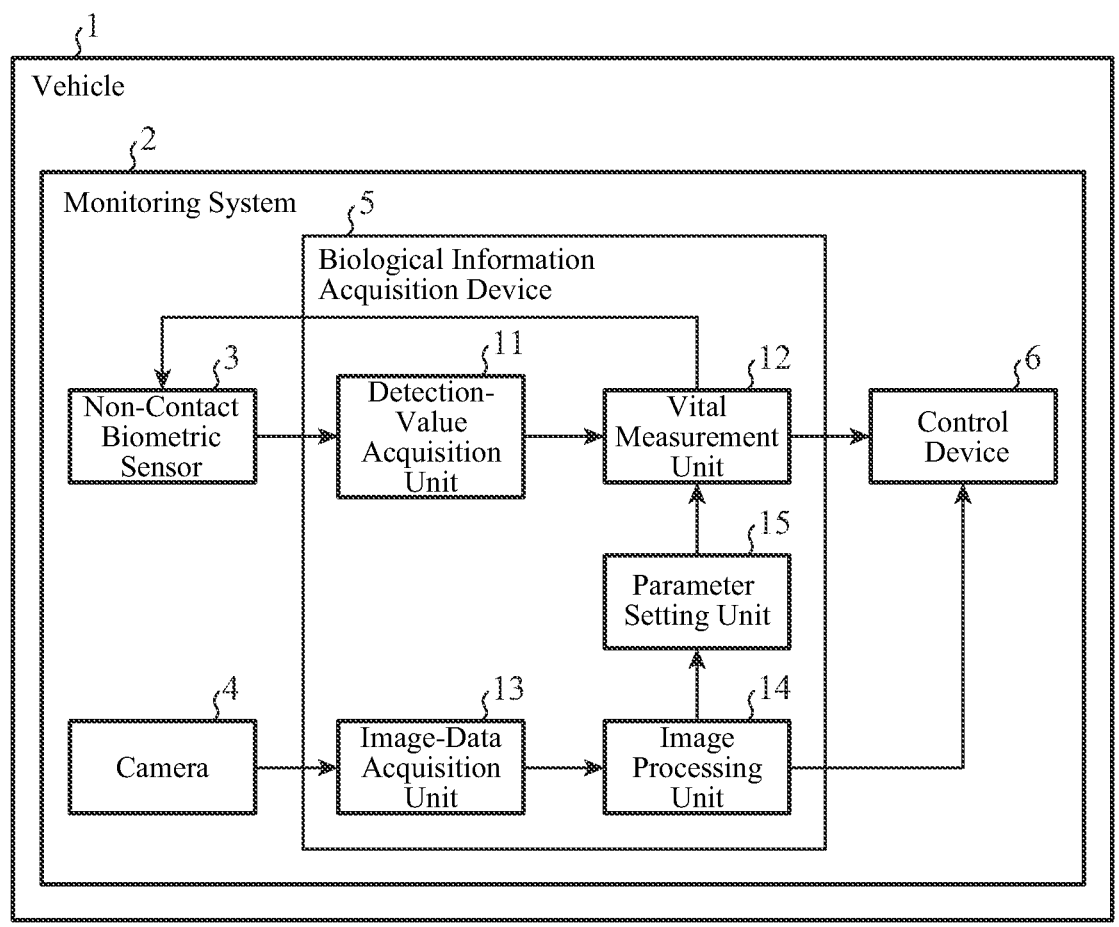
FIG. 1 is a block diagram illustrating a main part of a monitoring system including a biological information acquisition device according to a first embodiment.
Figure 2:
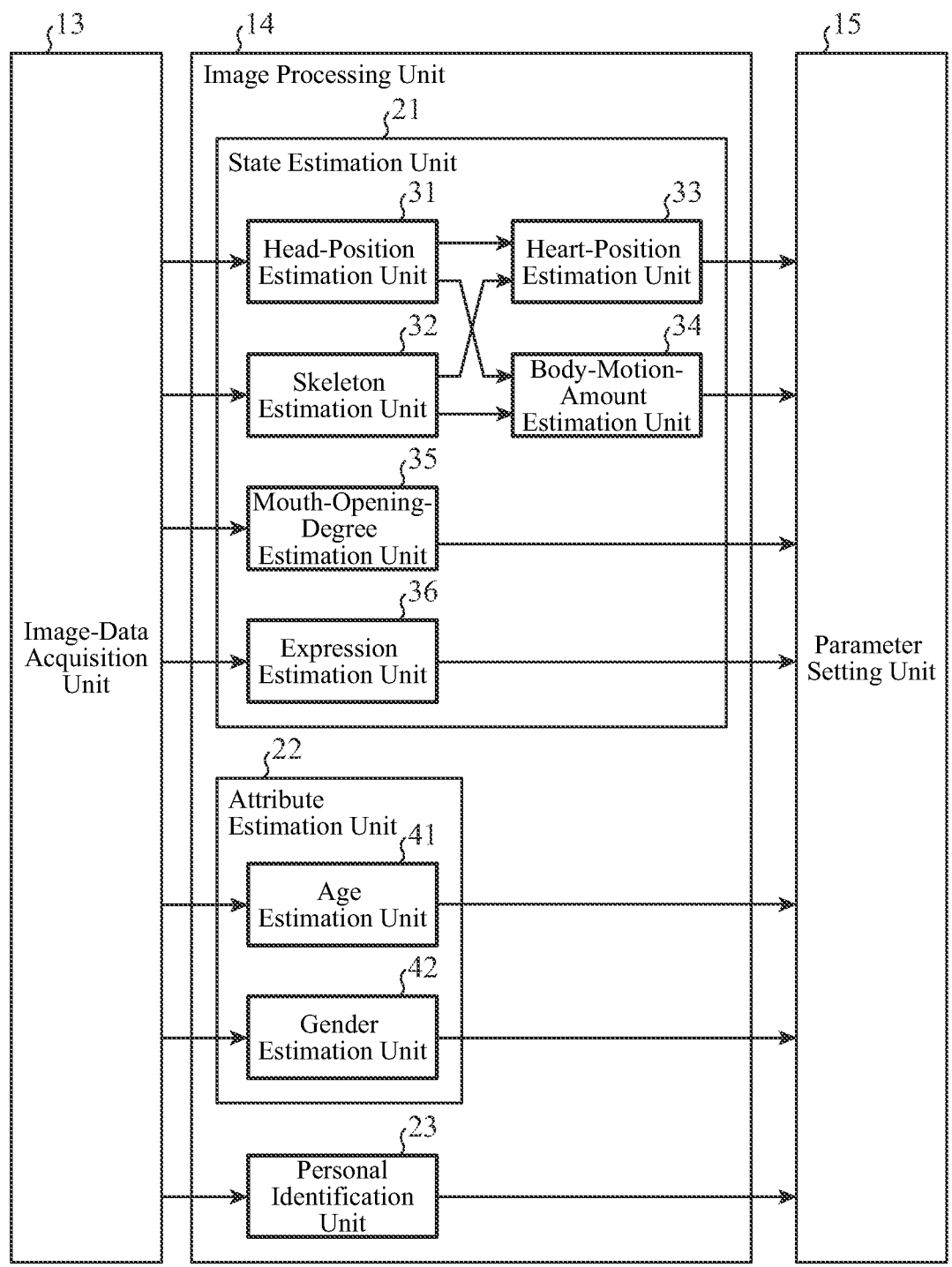
FIG. 2 is a block diagram illustrating a main part of an image processing unit in the biological information acquisition device according to the first embodiment.
Figure 3:
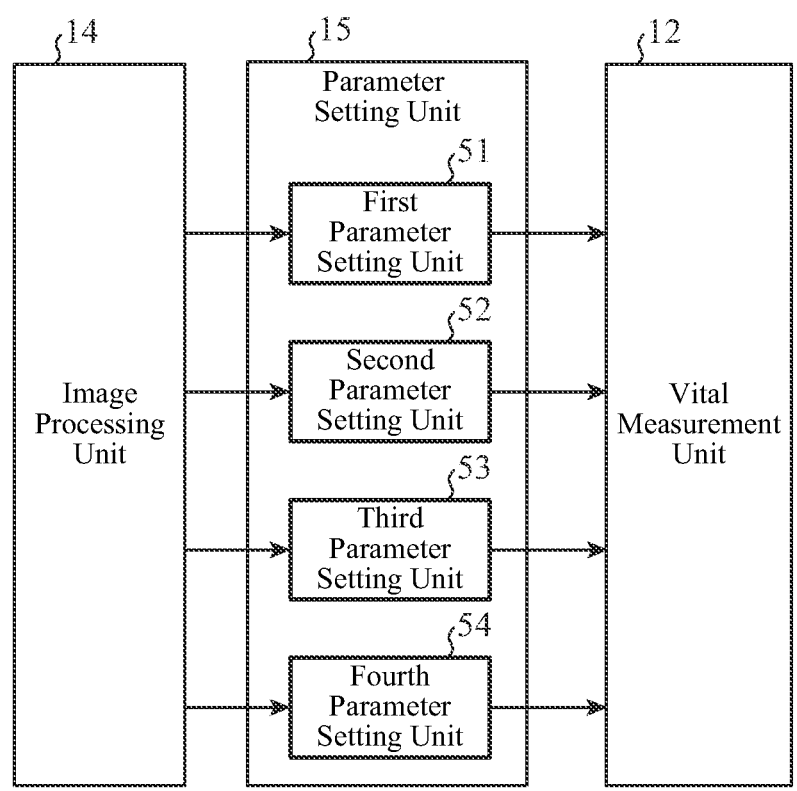
FIG. 3 is a block diagram illustrating a main part of a parameter setting unit in the biological information acquisition device according to the first embodiment.

FIG. 1 is a block diagram illustrating a main part of a monitoring system including a biological information acquisition device according to a first embodiment. FIG. 2 is a block diagram illustrating a main part of an image processing unit in the biological information acquisition device according to the first embodiment. FIG. 3 is a block diagram illustrating a main part of a parameter setting unit in the biological information acquisition device according to the first embodiment. The biological information acquisition device according to the first embodiment will be described with reference to FIGS. 1 to 3.

As illustrated in FIG. 1, a vehicle 1 includes a monitoring system 2. The monitoring system 2 includes a non-contact biometric sensor 3, a camera 4, a biological information acquisition device 5, and a control device 6. The biological information acquisition device 5 includes a detection-value acquisition unit 11, a vital measurement unit 12, an image-data acquisition unit 13, an image processing unit 14, and a parameter setting unit 15.

As illustrated in FIG. 2, the image processing unit 14 includes a state estimation unit 21, an attribute estimation unit 22, and a personal identification unit 23. The state estimation unit 21 includes a head-position estimation unit 31, a skeleton estimation unit 32, a heart-position estimation unit 33, a body-motion-amount estimation unit 34, a mouth-opening-degree estimation unit 35, and an expression estimation unit 36. The attribute estimation unit 22 includes an age estimation unit 41 and a gender estimation unit 42.

As illustrated in FIG. 3, the parameter setting unit 15 includes a first parameter setting unit 51, a second parameter setting unit 52, a third parameter setting unit 53, and a fourth parameter setting unit 54.

The monitoring system 2 includes a driver monitoring system (DMS) or an occupant monitoring system (OMS). That is, the monitoring system 2 monitors a driver sitting on a driver's seat of the vehicle 1. Alternatively, the monitoring system 2 monitors a passenger sitting on a passenger seat of the vehicle 1. Alternatively, the monitoring system 2 monitors each of the driver sitting on the driver's seat of the vehicle 1 and the passenger sitting on the passenger seat of the vehicle 1.

Hereinafter, a person to be monitored by the monitoring system 2 may be referred to as "target person". In addition, the target person may be denoted by reference sign "TP". That is, the target person TP is a person whose vital signs (including at least one of a heart rate or a respiratory rate; the same applies hereinafter) are to be measured using the non-contact biometric sensor 3. In addition, the target person TP is a person to be captured by the camera 4.

Hereinafter, the seat on which the target person TP is seated may be referred to as "target seat". In addition, the target seat may be denoted by reference sign "TS".

Figure 4A:
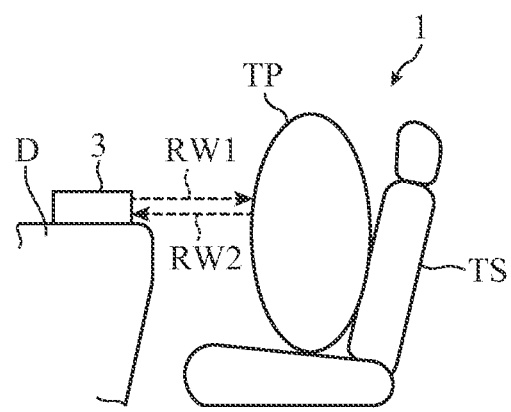
FIG. 4A is an explanatory diagram illustrating an example of installation positions of a non-contact biometric sensor and a camera in a vehicle, and is also an explanatory diagram illustrating a state as viewed from the left side of the vehicle.
Figure 4B:
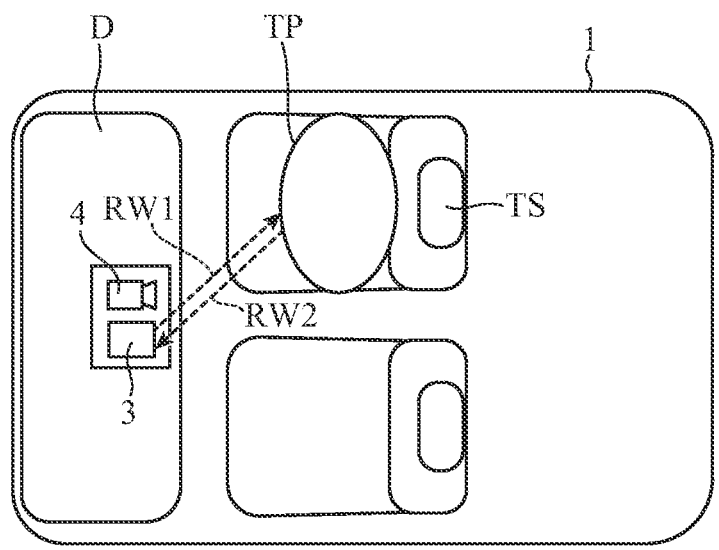
FIG. 4B is an explanatory diagram illustrating an example of the installation positions of the non-contact biometric sensor and the camera in the vehicle, and is also an explanatory diagram illustrating a state as viewed from above the vehicle.

The non-contact biometric sensor 3 includes, for example, a radio-wave non-contact biometric sensor for in-vehicle use. The non-contact biometric sensor 3 is installed, for example, on a dashboard D of the vehicle 1 or a steering column of the vehicle 1. FIG. 4 illustrates an example of an installation position of the non-contact biometric sensor 3 in the vehicle 1. In the drawing, RW1 indicates a radio wave transmitted by the non-contact biometric sensor 3. The target person TP is irradiated with the transmitted radio wave RW1. The irradiated radio wave RW1 is reflected by the target person TR. A reflected radio wave RW2 is received by the non-contact biometric sensor 3.

As a result, values for measuring vital signs are detected. Specifically, for example, values obtained by a Doppler radar, a frequency modulated continuous wave (FM-CW) radar, or a time-of-flight (ToF) device are detected. That is, a value corresponding to each frame is detected. Each frame corresponds to a predetermined time section.

Note that, in the example illustrated in FIG. 4, the non-contact biometric sensor 3 is disposed at the center of the vehicle 1 in a left-right direction. That is, the non-contact biometric sensor 3 is provided at a position between the driver's seat and the passenger seat on a dashboard D. However, the arrangement of the non-contact biometric sensor 3 is not limited to such an arrangement. The non-contact biometric sensor 3 is only required to be provided at a position where the target person TP is irradiated with the radio wave RW1 and the radio wave RW2 is received by the non-contact biometric sensor 3.

The camera 4 includes, for example, an in-vehicle infrared camera for capturing a video. The camera 4 is installed, for example, on the dashboard D. FIG. 4 illustrates an example of an installation position of the camera 4 in the vehicle 1. The camera 4 captures a range including the driver's seat of the vehicle 1, a range including the passenger seat of the vehicle 1, or a range including the driver's seat of the vehicle 1 and the passenger seat of the vehicle 1. As a result, the image captured by the camera 4 includes the target person TP when the target person TP is seated on the target seat TS. More specifically, the image captured by the camera 4 at this time includes at least the face of the target person TP.

Note that, in the example illustrated in FIG. 4, the camera 4 is disposed at the center of the vehicle 1 in the left-right direction. That is, the camera 4 is provided at the position between the driver's seat and the passenger seat on the dashboard D. However, the arrangement of the camera 4 is not limited to such an arrangement. The camera 4 is only required to be provided at a position where the target person TP is captured by the camera 4.

The detection-value acquisition unit 11 acquires a value (hereinafter, referred to as "detection value") detected by the non-contact biometric sensor 3. The detection-value acquisition unit 11 outputs the acquired detection value to the vital measurement unit 12.

The vital measurement unit 12 acquires the detection value output by the detection-value acquisition unit 11. The vital measurement unit 12 measures the vital signs of the target person TP using the acquired detection value. As a result, information (hereinafter, referred to as "biological information") indicating the measured vital signs is generated. The vital measurement unit 12 outputs the generated biological information to the control device 6.

Various known techniques can be used to measure vital signs by the vital measurement unit 12. Detailed description of these techniques will be omitted.

Here, measurement of vital signs by the vital measurement unit 12 is performed on the basis of a plurality of types of parameters. The plurality of types of parameters are set by the parameter setting unit 15 to be described later. The plurality of types of parameters include, for example, the following first parameter, second parameter, third parameter, and fourth parameter.

First Parameter

The vital measurement unit 12 can have a function of controlling the transmission direction of the radio wave RW1 by the non-contact biometric sensor 3 when measuring the vital signs of the target person TP. In other words, the vital measurement unit 12 can have a function of controlling a position (hereinafter, referred to as "irradiation position") irradiated with the radio wave RW1. Such a function will be described later with reference to FIGS. 10 and 11 in a second embodiment. The first parameter corresponds to the irradiation position.

Second Parameter

The vital measurement unit 12 has a function of selecting one or more frames among a plurality of temporally consecutive frames and using a detection value corresponding to the selected frame for vital measurement. The second parameter corresponds to a frame selected by the vital measurement unit 12 among the plurality of frames. That is, the second parameter corresponds to a frame (hereinafter, referred to as "measurement frame") used for measuring vital signs by the vital measurement unit 12 among the plurality of frames.

Third Parameter

The vital measurement unit 12 has a function of removing noise included in detection values corresponding to individual frames by performing a moving-average process on detection values corresponding to a plurality of temporally consecutive frames. The third parameter corresponds to a section width (hereinafter, referred to as "moving-average section width") in the moving-average process.

Fourth Parameter

The vital measurement unit 12 has a function of measuring vital signs within a predetermined numerical range. The fourth parameter corresponds to such a numerical range (hereinafter referred to as "measurement range").

The image-data acquisition unit 13 acquires image data indicating an image (hereinafter, "captured image") captured by the camera 4. The image-data acquisition unit 13 outputs the acquired image data to the image processing unit 14.

The image processing unit 14 acquires the image data output by the image-data acquisition unit 13. The image processing unit 14 performs a plurality of types of image processing on the captured image using the acquired image data. More specifically, each unit of the image processing unit 14 performs the corresponding image process as follows.

First, as described above, the captured image includes at least the face of the target person TP. The head-position estimation unit 31 detects a region (hereinafter, "face region") corresponding to the face of the target person TP in the captured image. Specifically, for example, the head-position estimation unit 31 detects a face region at each time. As a result, the head-position estimation unit 31 estimates the position of the head of (hereinafter, referred to as "head position") of the target person TP. Specifically, for example, the head-position estimation unit 31 detects a head position at each time.

The head-position estimation unit 31 outputs information (hereinafter, referred to as "face region information") indicating the detected face region to the heart-position estimation unit 33 and the body-motion-amount estimation unit 34. In addition, the head-position estimation unit 31 outputs information (hereinafter referred to as "head position information") indicating the estimated head position to the heart-position estimation unit 33 and the body-motion-amount estimation unit 34.

Various known techniques can be used to detect the face region by the head-position estimation unit 31. In addition, various known techniques can also be used to detect the head position by the head-position estimation unit 31. Detailed description of these techniques will be omitted.

Second, the captured image may include the upper body of the target person TP. In a case where the upper body of the target person TP is included in the captured image, the skeleton estimation unit 32 estimates the skeleton of the target person TP. Specifically, for example, the skeleton estimation unit 32 detects a skeleton at each time. The skeleton estimation unit 32 outputs information (hereinafter, referred to as "skeleton information") indicating the estimated skeleton to the heart-position estimation unit 33 and the body-motion-amount estimation unit 34.

Various known techniques can be used to estimate the skeleton by the skeleton estimation unit 32. Detailed description of these techniques will be omitted.

Thirdly, the heart-position estimation unit 33 acquires the face region information output by the head-position estimation unit 31 and the head position information output by the head-position estimation unit 31. The heart-position estimation unit 33 calculates a value corresponding to the distance between the top of the head of the target person TP and the bottom of the chin of the target person TP using the acquired face region information. The heart-position estimation unit 33 estimates the position (hereinafter referred to as "heart position") of the heart of the target person TP using the acquired head position information and the calculated value.

Alternatively, the heart-position estimation unit 33 acquires the skeleton information output by the skeleton estimation unit 32. The heart-position estimation unit 33 estimates the heart position of the target person TP using the acquired skeleton information.

The heart-position estimation unit 33 outputs information (hereinafter, referred to as "heart position information") indicating the estimated heart position (that is, the heart position estimated using the face region information and the head position information or the heart position estimated using the skeleton information) to the parameter setting unit 15. More specifically, the heart-position estimation unit 33 outputs the heart position information to the first parameter setting unit 51.

Here, the heart position may be represented by three distance values (x, y, z). x is a value indicating a distance in a depth direction based on the camera 4. y is a value indicating a distance in a vertical direction based on the camera 4. z is a value indicating a distance in the left-right direction based on the camera 4. For example, meter is used as the unit of each of the distance values (x, y, z).

Alternatively, the heart position may be represented by two angle values (yaw, pitch). yaw is a value indicating an angle in a yaw direction based on the camera 4. pitch is a value indicating an angle in a pitch direction based on the camera 4. For example, degree is used as the unit of each of the angle values (yaw, pitch).

In addition, various known techniques can be used to estimate the heart position by the heart-position estimation unit 33. Detailed description of these techniques will be omitted.

Fourth, the body-motion-amount estimation unit 34 acquires the face region information output by the head-position estimation unit 31. The body-motion-amount estimation unit 34 estimates the position (hereinafter referred to as "face position") of the face of the target person TP at each of a plurality of times included in each frame using the acquired face region information. The body-motion-amount estimation unit 34 calculates a change amount of the face position in each frame on the basis of the estimated face position. For example, meter per second is used as the unit of such a change amount.

Alternatively, the body-motion-amount estimation unit 34 acquires the head position information output by the head-position estimation unit 31. The body-motion-amount estimation unit 34 calculates a change amount of the head position in each frame on the basis of the estimated head position. For example, meter per second is used as the unit of such a change amount.

Alternatively, the body-motion-amount estimation unit 34 acquires the skeleton information output by the skeleton estimation unit 32. The body-motion-amount estimation unit 34 estimates the position (hereinafter, referred to as "body position") of the body of the target person TP at each of the plurality of times included in each frame using the acquired skeleton information. The body-motion-amount estimation unit 34 calculates a change amount of the body position in each frame on the basis of the estimated body position. For example, meter per second is used as the unit of such a change amount.

The body-motion-amount estimation unit 34 estimates the amount of body motion of the target person TP in each frame on the basis of the estimated change amount (that is, the change amount of the face position, the change amount of the head position, or the change amount of the body position). The body-motion-amount estimation unit 34 outputs information (hereinafter referred to as "body-motion-amount information") indicating the estimated amount of body motion to the parameter setting unit 15. More specifically, the body-motion-amount estimation unit 34 outputs the body-motion-amount information to the second parameter setting unit 52 and the third parameter setting unit 53.

In addition, various known techniques can be used to estimate the amount of body motion by the body-motion-amount estimation unit 34. Detailed description of these techniques will be omitted.

Fifth, the mouth-opening-degree estimation unit 35 estimates the degree of mouth opening of the target person TP. Specifically, for example, the mouth-opening-degree estimation unit 35 estimates the degree of mouth opening in each frame. The mouth-opening-degree estimation unit 35 outputs information (hereinafter, referred to as "mouth-opening-degree information") indicating the estimated degree of mouth opening to the parameter setting unit 15. More specifically, the mouth-opening-degree estimation unit 35 outputs the mouth-opening-degree information to the second parameter setting unit 52 and the third parameter setting unit 53.

Various known techniques can be used to estimate the degree of mouth opening by the mouth-opening-degree estimation unit 35. Detailed description of these techniques will be omitted.

Sixth, the expression estimation unit 36 estimates the expression of the target person TP. As a result, a value (hereinafter, referred to as "expression value") corresponding to the expression of the target person TP is calculated. The expression estimation unit 36 outputs information (hereinafter, referred to as "expression information") indicating the estimated expression, that is, information including the calculated expression value, to the parameter setting unit 15. More specifically, the expression estimation unit 36 outputs the expression information to the fourth parameter setting unit 54.

Various known techniques can be used to estimate the expression by the expression estimation unit 36. Detailed description of these techniques will be omitted.

Seventh, the age estimation unit 41 estimates the age of the target person TP. The age estimation unit 41 outputs information (hereinafter, referred to as "age information") indicating the estimated age to the parameter setting unit 15. More specifically, the age estimation unit 41 outputs the age information to the fourth parameter setting unit 54.

Various known techniques can be used to estimate the age by the age estimation unit 41. Detailed description of these techniques will be omitted.

Eighth, the gender estimation unit 42 estimates the gender of the target person TP. The gender estimation unit 42 outputs information (hereinafter, referred to as "gender information") indicating the estimated gender to the parameter setting unit 15. More specifically, the gender estimation unit 42 outputs the gender information to the fourth parameter setting unit 54.

Various known techniques can be used to estimate a gender by the gender estimation unit 42. Detailed description of these techniques will be omitted.

Ninth, the personal identification unit 23 identifies the target person TP using information registered in a predetermined database (hereinafter, referred to as "personal identification database"). That is, in a case where the vehicle 1 is used by a plurality of users, the personal identification unit 23 specifies which user among the plurality of users is the current target person TP. The personal identification unit 23 acquires information related to the identified target person TP, that is, information related to the specified user (hereinafter referred to as "personal identification information") from the personal identification database. The personal identification unit 23 outputs the acquired personal identification information to the parameter setting unit 15. More specifically, the personal identification unit 23 outputs the personal identification information to the first parameter setting unit 51 and the fourth parameter setting unit 54.

Various known techniques can be used to identify the target person TP by the personal identification unit 23. Detailed description of these techniques will be omitted.

Here, the personal identification information includes information indicating the heart position of the identified target person TP. Such information is generated by the heart-position estimation unit 33, for example, when the specified user has gotten on the vehicle 1 in the past. Alternatively, such information is input in advance by the specified user, for example.

In addition, the personal identification information includes information indicating the age of the identified target person TP. Such information is generated by the age estimation unit 41, for example, when the specified user has boarded the vehicle 1 in the past. Alternatively, such information is input in advance by the specified user, for example.

In addition, the personal identification information includes information indicating the gender of the identified target person TP. Such information is generated by the gender estimation unit 42, for example, when the specified user has boarded the vehicle 1 in the past. Alternatively, such information is input in advance by the specified user, for example.

As described above, the information output from the image processing unit 14 to the parameter setting unit 15 includes the heart position information, the body-motion-amount information, the mouth-opening-degree information, the expression information, the age information, the gender information, and the personal identification information. The image processing unit 14 outputs at least some of these pieces of information to the control device 6.

Note that the estimation of the state of the target person TP includes the detection of the face region, the estimation of the head position, the estimation of the skeleton, the estimation of the heart position, the estimation of the amount of body motion, the estimation of the degree of mouth opening, and the estimation of the expression. That is, the state estimation unit 21 estimates the state of the target person TP. Furthermore, the estimation of attributes of the target person TP includes the estimation of the age and the estimation of the gender. That is, the attribute estimation unit 22 estimates the attributes of the target person TP.

The parameter setting unit 15 acquires the information output from the image processing unit 14 (including the heart position information, the body-motion-amount information, the mouth-opening-degree information, the expression information, the age information, the gender information, and the personal identification information). The parameter setting unit 15 sets a plurality of types of parameters in the vital measurement unit 12 using these pieces of information. FIG. 5 is an explanatory diagram illustrating a correspondence relationship between information output by the image processing unit 14 and parameters set by the parameter setting unit 15. The plurality of types of parameters are set as follows.

Method of Setting First Parameter

First, the first parameter setting unit 51 acquires the heart position information output by the heart-position estimation unit 33. The first parameter setting unit 51 sets the first parameter in the vital measurement unit 12 using the acquired heart position information.

That is, the first parameter setting unit 51 sets the vital measurement unit 12 so as to control the irradiation position of the radio wave RW1 to a position corresponding to the heart position indicated by the acquired heart position information. As a result, the irradiation position of the radio wave RW1 can be adjusted to a position suitable for measuring vital signs (particularly, a heart rate). Such adjustment will be described later with reference to FIGS. 10 and 11 in the second embodiment.

Alternatively, the first parameter setting unit 51 includes the personal identification information output by the personal identification unit 23. The first parameter setting unit 51 sets the first parameter in the vital measurement unit 12 using the acquired personal identification information.

That is, as described above, the personal identification information includes the information indicating the heart position of the target person TP. The first parameter setting unit 51 sets the vital measurement unit 12 so as to control the irradiation position of the radio wave RW1 to a position corresponding to the heart position indicated by the heart position information. As a result, the irradiation position of the radio wave RW1 can be adjusted to a position suitable for measuring vital signs (particularly, a heart rate). Such adjustment will be described later with reference to FIGS. 10 and 11 in the second embodiment.

Note that the first parameter setting unit 51 may acquire the heart position information and the personal identification information. The first parameter setting unit 51 may set the first parameter by selectively using any one of the acquired heart position information and the acquired personal identification information.

Method of Setting Second Parameter

Second, the second parameter setting unit 52 acquires the body-motion-amount information output by the body-motion-amount estimation unit 34. The second parameter setting unit 52 sets the second parameter in the vital measurement unit 12 using the acquired body-motion-amount information.

That is, the second parameter setting unit 52 sets the vital measurement unit 12 so as to select a frame corresponding to the amount of body motion less than or equal to a predetermined threshold Th1 as a measurement frame. In other words, the second parameter setting unit 52 sets the vital measurement unit 12 so as to exclude a frame corresponding to the amount of body motion exceeding the threshold. Th1 from those for vital sign measurement. As a result, it is possible to achieve adjustment that prevents a frame unsuitable for vital sign measurement (that is, a frame in a case where the target person TP moves the body) from being used for vital sign measurement.

Alternatively, the second parameter setting unit 52 acquires the mouth-opening-degree information output by the mouth-opening-degree estimation unit 35. The second parameter setting unit 52 sets the second parameter in the vital measurement unit 12 using the acquired mouth-opening-degree information.

That is, the second parameter setting unit 52 sets the vital measurement unit 12 so as to select a frame corresponding to the degree of mouth opening less than or equal to a predetermined threshold Th2 as the measurement frame. In other words, the second parameter setting unit 52 sets the vital measurement unit 12 so as to exclude a frame corresponding to the degree of mouth opening exceeding the threshold Th2 from those for vital sign measurement. As a result, it is possible to achieve adjustment that prevents a frame unsuitable for vital sign measurement (that is, a frame in a case where the target person TP is in conversation) from being used for vital sign measurement.

Note that the second parameter setting unit 52 may acquire the body-motion-amount information and the mouth-opening-degree information, and set the second parameter using the acquired body-motion-amount information and the acquired mouth-opening-degree information. In this case, the second parameter setting unit 52 may set the vital measurement unit 12 so as to select, as the measurement frame, a frame corresponding to the amount of body motion less than or equal to the threshold Th1 and corresponding to the degree of mouth opening less than or equal to the threshold Th2.

Method of Setting Third Parameter

Third, the third parameter setting unit 53 acquires the body-motion-amount information output by the body-motion-amount estimation unit 34. The third parameter setting unit 53 sets the third parameter in the vital measurement unit 12 using the acquired body-motion-amount information.

That is, the third parameter setting unit 53 calculates the number n of frames corresponding to the amount of body motion less than or equal to a predetermined threshold Th3 for a plurality of frames corresponding to a predetermined time (including one frame for which the average value is calculated in the moving average process). The third parameter setting unit 53 calculates a ratio R1 of the calculated number n to the number N of the plurality of frames (R1=n/N). In a case where the calculated ratio R1 is large, the third parameter setting unit 53 sets the vital measurement unit 12 so as to reduce the corresponding moving average section width. On the other hand, in a case where the calculated ratio R1 is small, the third parameter setting unit 53 sets the vital measurement unit 12 so as to increase the corresponding moving average section width. As a result, the moving average section width can be adjusted to a suitable width depending on the amount of body motion.

Alternatively, the third parameter setting unit 53 acquires the mouth-opening-degree information output by the mouth-opening-degree estimation unit 35. The third parameter setting unit 53 sets the third parameter in the vital measurement unit 12 using the acquired mouth-opening-degree information.

That is, the third parameter setting unit 53 calculates the number m of frames corresponding to the degree of mouth opening less than or equal to a predetermined threshold Th4 for a plurality of frames corresponding to a predetermined time (including one frame for which the average value is calculated in the moving average process). The third parameter setting unit 53 calculates a ratio R2 of the calculated number m to the number M of the plurality of frames (R2=m/M). In a case where the calculated ratio R2 is large, the third parameter setting unit 53 sets the vital measurement unit 12 so as to reduce the corresponding moving average section width. On the other hand, in a case where the calculated ratio R2 is small, the third parameter setting unit 53 sets the vital measurement unit 12 so as to increase the corresponding moving average section width. As a result, the moving average section width can be adjusted to a suitable width depending on the degree of mouth opening.

Note that the third parameter setting unit 53 may acquire the body-motion-amount information and the mouth-opening-degree information, and set the third parameter using the acquired body-motion-amount information and the acquired mouth-opening-degree information. In this case, the third parameter setting unit 53 may calculate the ratios R1 and R2, and set the vital measurement unit 12 so as to adjust the moving average section width depending on a statistical value (for example, a total value or an average value) based on the calculated ratios R1 and R2.

Method of Setting Fourth Parameter

Fourth, the fourth parameter setting unit 54 acquires the expression information output by the expression estimation unit 36. The fourth parameter setting unit 54 sets the fourth parameter in the vital measurement unit 12 using the acquired expression information.

That is, the fourth parameter setting unit 54 estimates the degree of excitement of the target person TP on the basis of an expression value included in the acquired expression information. In a case where the estimated degree of excitement is high, the fourth parameter setting unit 54 sets the vital measurement unit 12 so as to use a numerical range including a higher numerical value as the measurement range. On the other hand, in a case where the estimated degree of excitement is low, the fourth parameter setting unit 54 sets the vital measurement unit 12 so as to use a numerical range including a lower numerical value as the measurement range.

Alternatively, the fourth parameter setting unit 54 acquires the age information output by the age estimation unit 41. The fourth parameter setting unit 54 sets the fourth parameter in the vital measurement unit 12 using the acquired age information.

That is, standard vital signs typically vary with age. More specifically, the numerical value gradually decreases as the age increases. Therefore, a table indicating a correspondence relationship between a plurality of age groups and a plurality of numerical ranges related to vital signs is prepared in advance. The fourth parameter setting unit 54 selects a numerical range corresponding to the age group including the age indicated by the acquired age information among the plurality of numerical ranges. The fourth parameter setting unit 54 sets the vital measurement unit 12 so as to use the selected numerical range as the measurement range.

Alternatively, the fourth parameter setting unit 54 acquires the gender information output by the gender estimation unit 42. The fourth parameter setting unit 54 sets the fourth parameter in the vital measurement unit 12 using the acquired gender information.

That is, standard vital signs typically vary with gender. Therefore, a table indicating a correspondence relationship between a plurality of genders and a plurality of numerical ranges related to vital signs is prepared in advance. The fourth parameter setting unit 54 selects a numerical range corresponding to the gender indicated by the acquired gender information among the plurality of numerical ranges. The fourth parameter setting unit 54 sets the vital measurement unit 12 so as to use the selected numerical range as the measurement range.

Note that the fourth parameter setting unit 54 may acquire the age information and the gender information, and set the fourth parameter using the acquired age information and the acquired gender information. For example, a table indicating a correspondence relationship among a plurality of age groups, a plurality of genders, and a plurality of numerical ranges related to vital signs is prepared in advance. The fourth parameter setting unit 54 selects a numerical range corresponding to the age group including the age indicated by the acquired age information and corresponding to the gender indicated by the acquired gender information among the plurality of numerical ranges. The fourth parameter setting unit 54 sets the vital measurement unit 12 so as to use the selected numerical range as the measurement range.

Alternatively, the fourth parameter setting unit 54 may acquire the expression information and the age information, and set the fourth parameter using the acquired expression information and the acquired age information. For example, the fourth parameter setting unit 54 corrects (for example, shifts, enlarges, or reduces) the numerical range selected on the basis of the age information depending on the degree of excitement. The fourth parameter setting unit 54 sets the vital measurement unit 12 so as to use the corrected numerical range as the measurement range.

Alternatively, the fourth parameter setting unit 54 may acquire the expression information and the gender information, and set the fourth parameter using the acquired expression information and the acquired gender information. For example, the fourth parameter setting unit 54 corrects (for example, shifts, enlarges, or reduces) the numerical range selected on the basis of the gender information depending on the degree of excitement. The fourth parameter setting unit 54 sets the vital measurement unit 12 so as to use the corrected numerical range as the measurement range.

Alternatively, the fourth parameter setting unit 54 acquires the personal identification information output by the personal identification unit 23. The fourth parameter setting unit 54 sets the fourth parameter in the vital measurement unit 12 using the acquired personal identification information.

That is, as described above, the personal identification information includes information indicating the age of the target person TP and information indicating the gender of the target person TP. Therefore, the fourth parameter setting unit 54 sets the fourth parameter using the information indicating the age by a setting method similar to the setting method using the age information. Alternatively, the fourth parameter setting unit 54 sets the fourth parameter using the information indicating the gender by a setting method similar to the setting method using the gender information. Alternatively, the fourth parameter setting unit 54 sets the fourth parameter using the information indicating the age and the information indicating the gender by a setting method similar to the setting method using the age information and the gender information.

Note that the fourth parameter setting unit 54 may acquire the expression information and the personal identification information, and set the fourth parameter using the acquired expression information and the acquired personal identification information. For example, the fourth parameter setting unit 54 sets the fourth parameter using the expression information and the information indicating the age included in the personal identification information by a setting method similar to the setting method using the expression information and the age information. Alternatively, the fourth parameter setting unit 54 sets the fourth parameter using the expression information and the information indicating the gender included in the personal identification information by a setting method similar to the setting method using the expression information and the gender information. Alternatively, the fourth parameter setting unit 54 sets the fourth parameter using the expression information, and the information indicating the age and the information indicating the gender included in the personal identification information by a setting method similar to the setting method using the expression information, the age information, and the gender information.

In this way, the main part of the biological information acquisition device 5 is configured.

The control device 6 includes, for example, an electronic control unit (ECU). The control device 6 acquires biological information output by the vital measurement unit 12 and also acquires information output by the image processing unit 14. The control device 6 executes various types of control for DMS or various types of control for OMS by using these pieces of information.

For example, the control device 6 monitors an awakening level and the degree of comfort of the driver among the target persons TP using these pieces of information. When the awakening level decreases, the control device 6 executes control to output a warning to the driver or control to stop the vehicle 1 by operating the vehicle 1. When the degree of comfort decreases, the control device 6 executes control to operate the equipment (for example, an air conditioner) of the vehicle 1.

In addition, for example, the control device 6 monitors the degree of comfort of a passenger among the target persons TP using these pieces of information. When the degree of comfort decreases, the control device 6 executes control to operate the equipment (for example, an air conditioner) of the vehicle 1.

In addition, various known techniques can be used to execute control for DMS by the control device 6. Furthermore, various known techniques can be used to execute control for OMS by the control device 6. Detailed description of these techniques will be omitted.

Hereinafter, the process performed by the detection-value acquisition unit 11 may be collectively referred to as "detection-value acquisition process". Furthermore, the process performed by the vital measurement unit 12 may be collectively referred to as "vital measurement process". In addition, the process performed by the image-data acquisition unit 13 may be collectively referred to as "image-data acquisition process". Further, the process performed by the parameter setting unit 15 may be collectively referred to as "parameter setting process". Furthermore, the process performed by the state estimation unit 21 may be collectively referred to as "state estimation process". Further, the process performed by the attribute estimation unit 22 may be collectively referred to as "attribute estimation process". Furthermore, the process performed by the personal identification unit 23 may be collectively referred to as "personal identification process".

Hereinafter, the function of the detection-value acquisition unit 11 may be denoted by reference sign "F1". In addition, the function of the vital measurement unit 12 may be denoted by reference sign "F2". Moreover, the function of the image-data acquisition unit 13 may be denoted by reference sign "F3". Furthermore, the function of the image processing unit 14 may be denoted by reference sign "F4". Moreover, the function of the parameter setting unit 15 may be denoted by reference sign "F5".

Next, a hardware configuration of the main part of the biological information acquisition device 5 will be described with reference to FIGS. 6 to 8.

Figure 6:
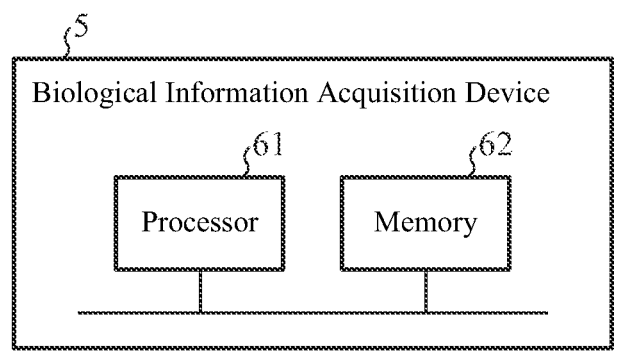
FIG. 6 is a block diagram illustrating a hardware configuration of a main part of the biological information acquisition device according to the first embodiment.

As illustrated in FIG. 6, the biological information acquisition device 5 includes a processor 61 and a memory 62. The memory 62 stores programs corresponding to the plurality of functions F1 to F5. The processor 61 reads and executes the program stored in the memory 62. As a result, the plurality of functions F1 to F5 are implemented.

Figure 7:
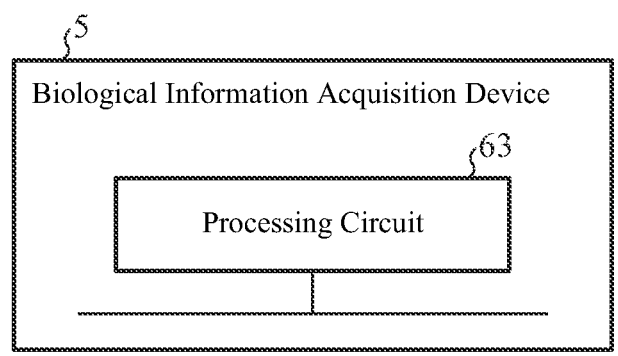
FIG. 7 is a block diagram illustrating another hardware configuration of the main part of the biological information acquisition device according to the first embodiment.

Alternatively, as illustrated in FIG. 7, the biological information acquisition device 5 includes a processing circuit 63. The processing circuit 63 performs the processes corresponding to the plurality of functions F1 to F5. As a result, the plurality of functions F1 to F5 are implemented.

Figure 8:
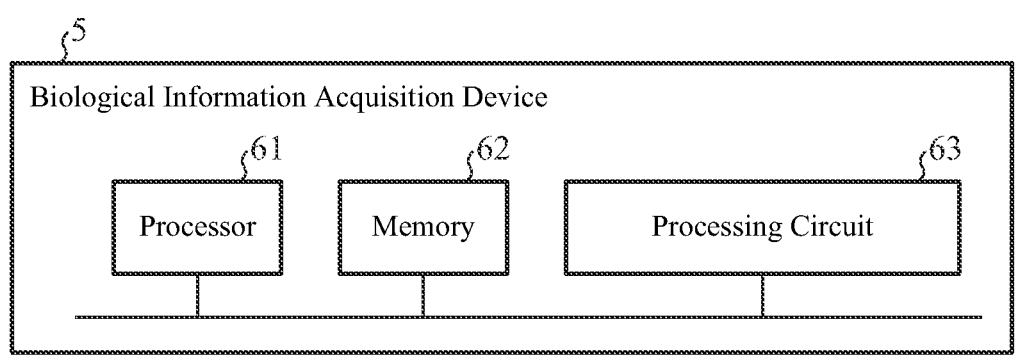
FIG. 8 is a block diagram illustrating yet another hardware configuration of the main part of the biological information acquisition device according to the first embodiment.

Alternatively, as illustrated in FIG. 8, the biological information acquisition device 5 includes the processor 61, the memory 62, and the processing circuit 63. The memory 62 stores a program corresponding to some of the plurality of functions F1 to F5. The processor 61 reads and executes the program stored in the memory 62. As a result, some of such functions are implemented. In addition, the processing circuit 63 performs the process corresponding to the remaining of the plurality of functions F1 to F5. As a result, the remaining function is implemented.

The processor 61 includes one or more processors. Each processor uses, for example, a central processing unit (CPU), a graphics processing unit (GPU), a microprocessor, a microcontroller, or a digital signal processor (DSP).

The memory 62 includes one or more nonvolatile memories. Alternatively, the memory 62 includes one or more nonvolatile memories and one or more volatile memories. That is, the memory 62 includes one or more memories. Each memory uses, for example, a semiconductor memory or a magnetic disk. More specifically, each volatile memory uses, for example, a random access memory (RAM). In addition, each nonvolatile memory uses, for example, a read only memory (ROM), a flash memory, an erasable programmable read only memory (EPROM), an electrically erasable programmable read only memory (EEPROM), a solid state drive, or a hard disk drive.

The processing circuit 63 includes one or more digital circuits. Alternatively, the processing circuit 63 includes one or more digital circuits and one or more analog circuits. That is, the processing circuit 63 includes one or more processing circuits. Each processing circuit uses, for example, an application specific integrated circuit (ASIC), a programmable logic device (PLD), a field programmable gate array (FPGA), a system on a chip (SoC), or a system large scale integration (LSI).

Here, when the processor 61 includes a plurality of processors, the correspondence relationship between the plurality of functions F1 to F5 and the plurality of processors is freely determined. That is, each of the plurality of processors can read and execute a program corresponding to one or more corresponding functions among the plurality of functions F1 to F5. The processor 61 can include dedicated processors corresponding to the individual functions F1 to F5.

In addition, when the memory 62 includes a plurality of memories, the correspondence relationship between the plurality of functions F1 to F5 and the plurality of memories is freely determined. That is, each of the memories can store a program corresponding to one or more corresponding functions among the plurality of functions F1 to F5. The memory 62 can include dedicated memories corresponding to the individual functions F1 to F5.

In addition, when the processing circuit 63 includes a plurality of processing circuits, the correspondence relationship between the plurality of functions F1 to F5 and the plurality of processing circuits is freely determined. That is, each of the plurality of processing circuits can perform a process corresponding to one or more corresponding functions among the plurality of functions F1 to F5. The processing circuit 63 can include dedicated processing circuits corresponding to the individual functions F1 to F5.

Figure 9A:
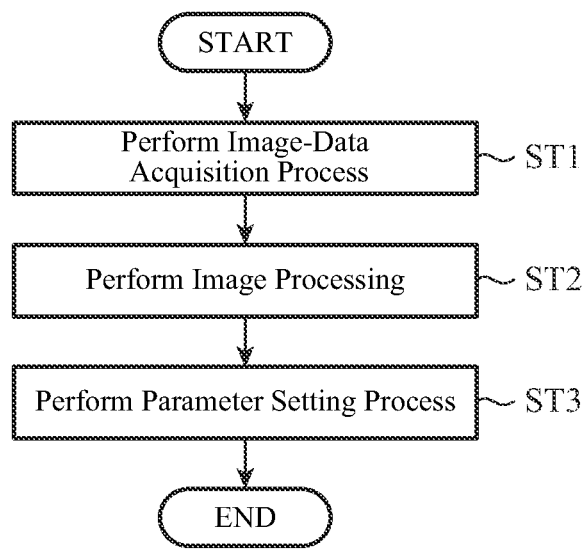
FIG. 9A is a flowchart illustrating an operation of the biological information acquisition device according to the first embodiment.

Next, an operation of the biological information acquisition device 5 will be described focusing on operations of the image-data acquisition unit 13, the image processing unit 14, and the parameter setting unit 15 with reference to a flowchart illustrated in FIG. 9A.

First, the image-data acquisition unit 13 performs the image-signal acquisition process (step ST1). As a result, image data indicating an image captured by the camera 4 is acquired.

Next, the image processing unit 14 performs a plurality of types of image processing (step ST2). As a result, the state estimation process, the attribute estimation process, and the personal identification process are performed.

Next, the parameter setting unit 15 performs the parameter setting process (step ST3). As a result, a plurality of types of parameters in the vital measurement unit 12 are set. Specifically, for example, the first parameter, the second parameter, the third parameter, and the fourth parameter are set.

Figure 9B:
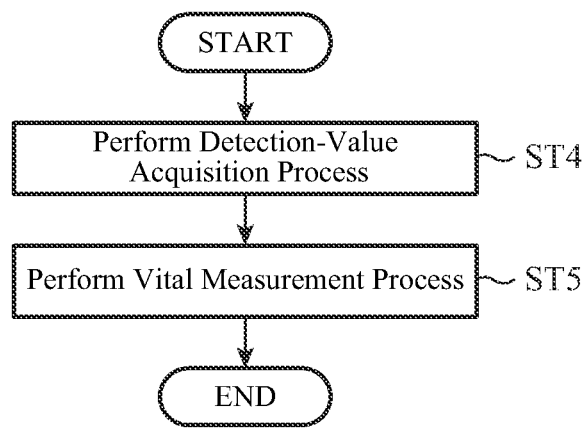
FIG. 9B is a flowchart illustrating an operation of the biological information acquisition device according to the first embodiment.

Next, the operation of the biological information acquisition device 5 will be described focusing on operations of the detection-value acquisition unit 11 and the vital measurement unit 12 with reference to a flowchart of FIG. 9B.

First, the detection-value acquisition unit 11 performs the detection-value acquisition process (step ST4). As a result, a detection value from the non-contact biometric sensor 3 is acquired.

Next, the vital measurement unit 12 performs the vital measurement process (step ST5). As a result, vital signs of the target person TP are measured and biological information is generated. At this time, the vital measurement unit 12 measures the vital signs of the target person TP on the basis of the plurality of types of parameters set in step ST3.

Next, effects of the biological information acquisition device 5 will be described.

First, in the conventional technique, the directivity of a non-contact biometric sensor is adjusted depending on the position of a seat (more specifically, a driver's seat) in a vehicle. On the other hand, in the biological information acquisition device 5, the first parameter (that is, the irradiation position of the radio wave RW1) is adjusted in accordance with the result of the image processing (more specifically, the state estimation process or the personal identification process). The target position (for example, the heart position) can be more accurately irradiated with the radio wave RW1 by the adjustment in accordance with to the result of the image processing as compared with the adjustment depending on the position of the seat.

Second, it is possible to achieve adjustment of various parameters by the adjustment in accordance with the result of the image processing, as compared with the adjustment depending on the position of the seat. For example, not only the irradiation position can be adjusted, but also the measurement frame, the moving average section width, and the measurement range can be adjusted.

Third, since the image processing includes the attribute estimation process and the personal identification process, it is possible to achieve adjustment of a plurality of types of parameters in consideration of individual differences. Specifically, for example, it is possible to achieve the adjustment of the first parameter and the fourth parameter in consideration of individual differences.

These effects can improve the measurement accuracy of the vital signs.

Next, a modification of the biological information acquisition device 5 will be described.

The parameter setting unit 15 does not need to include the first parameter setting unit 51. In this case, the image processing unit 14 does not need to include the heart-position estimation unit 33.

Alternatively, the parameter setting unit 15 does not need to include the second parameter setting unit 52.

Alternatively, the parameter setting unit 15 does not need to include the third parameter setting unit 53.

Alternatively, the parameter setting unit 15 does not need to include the fourth parameter setting unit 54. In this case, the image processing unit 14 does not need to include the expression estimation unit 36, the age estimation unit 41, and the gender estimation unit 42.

Alternatively, the parameter setting unit 15 does not need to include the first parameter setting unit 51 and the second parameter setting unit 52. In this case, the image processing unit 14 does not need to include the heart-position estimation unit 33.

Alternatively, the parameter setting unit 15 does not need to include the first parameter setting unit 51 and the third parameter setting unit 53. In this case, the image processing unit 14 does not need to include the heart-position estimation unit 33.

Alternatively, the parameter setting unit 15 does not need to include the first parameter setting unit 51 and the fourth parameter setting unit 54. In this case, the image processing unit 14 does not need to include the heart-position estimation unit 33, the expression estimation unit 36, the age estimation unit 41, the gender estimation unit 42, and the personal identification unit 23.

Alternatively, the parameter setting unit 15 does not need to include the second parameter setting unit 52 and the third parameter setting unit 53. In this case, the image processing unit 14 does not need to include the body-motion-amount estimation unit 34 and the mouth-opening-degree estimation unit 35.

Alternatively, the parameter setting unit 15 does not need to include the second parameter setting unit 52 and the fourth parameter setting unit 54. In this case, the image processing unit 14 does not need to include the expression estimation unit 36, the age estimation unit 41, and the gender estimation unit 42.

Alternatively, the parameter setting unit 15 does not need to include the third parameter setting unit 53 and the fourth parameter setting unit 54. In this case, the image processing unit 14 does not need to include the expression estimation unit 36, the age estimation unit 41, and the gender estimation unit 42.

Alternatively, the parameter setting unit 15 does not need to include the first parameter setting unit 51, the second parameter setting unit 52, and the third parameter setting unit 53. In this case, the image processing unit 14 does not need to include the head-position estimation unit 31, the skeleton estimation unit 32, the heart-position estimation unit 33, the body-motion-amount estimation unit 34, and the mouth-opening-degree estimation unit 35.

Alternatively, the parameter setting unit 15 does not need to include the first parameter setting unit 51, the second parameter setting unit 52, and the fourth parameter setting unit 54. In this case, the image processing unit 14 does not need to include the heart-position estimation unit 33, the expression estimation unit 36, the age estimation unit 41, the gender estimation unit 42, and the personal identification unit 23.

Alternatively, the parameter setting unit 15 does not need to include the first parameter setting unit 51, the third parameter setting unit 53, and the fourth parameter setting unit 54. In this case, the image processing unit 14 does not need to include the heart-position estimation unit 33, the expression estimation unit 36, the age estimation unit 41, the gender estimation unit 42, and the personal identification unit 23.

Alternatively, the parameter setting unit 15 does not need to include the second parameter setting unit 52, the third parameter setting unit 53, and the fourth parameter setting unit 54. In this case, the image processing unit 14 does not need to include the body-motion-amount estimation unit 34, the mouth-opening-degree estimation unit 35, the expression estimation unit 36, the age estimation unit 41, and the gender estimation unit 42.

That is, the parameter setting unit 15 may set at least one of the first parameter, the second parameter, the third parameter, or the fourth parameter. Furthermore, the image processing unit 14 may include at least one of the state estimation unit 21, the attribute estimation unit 22, or the personal identification unit 23. In other words, the image processing unit 14 may perform at least one of the state estimation process, the attribute estimation process, or the personal identification process. Furthermore, the state estimation process may include at least one of a process of estimating a heart position, a process of estimating the amount of body motion, a process of estimating the degree of mouth opening, or a process of estimating an expression. Further, the attribute estimation process may include at least one of a process of estimating age or a process of estimating gender.

Next, another modification of the biological information acquisition device 5 will be described.

Information indicating vital signs measured by the vital measurement unit 12 (that is, biological information) may be registered in a personal identification database. The registered biological information may be used for the next and subsequent personal identification processes.

Next, yet another modification of the biological information acquisition device 5 will be described.

Sensors (not illustrated) may be mounted on the vehicle 1. The sensors include, for example, a sensor (hereinafter, referred to as "seat position sensor") that detects the position of the target seat TS in the vehicle 1. In addition, the sensors include, for example, a sensor (hereinafter, referred to as "steering angle sensor") that detects the steering angle of the vehicle 1.

When estimating the heart position of the target person TP, the heart-position estimation unit 33 may use a value detected by the seat position sensor in addition to the information (that is, the face region information and the head position information) output by the head-position estimation unit 31 or the information (that is, the skeleton information) output by the skeleton estimation unit 32. As a result, the estimation accuracy of the heart position can be improved.

When estimating the amount of body motion of the target person TP, the body-motion-amount estimation unit 34 may use a value detected by the steering angle sensor in addition to the information (that is, the face region information or the head position information) output by the head-position estimation unit 31 or the information (that is, the skeleton information) output by the skeleton estimation unit 32. As a result, the estimation accuracy of the amount of body motion can be improved.

Next, yet another modification of the biological information acquisition device 5 will be described.

The biological information acquisition device 5 may use a non-contact biometric sensor 3 of another type instead of the radio-wave non-contact biometric sensor 3. For example, the non-contact biometric sensor 3 may use light, laser, or ultrasonic waves instead of radio waves. Hereinafter, radio waves, light, lasers, ultrasonic waves, or the like may be collectively referred to as "measurement waves".

Next, still another modification of the biological information acquisition device 5 will be described.

The application of the biological information acquisition device 5 is not limited to DMS or OMS. That is, the non-contact biometric sensor 3 and the camera 4 are not limited to those for in-vehicle use. In addition, the target person TP is not limited to the passenger of the vehicle 1. The biological information acquisition device 5 may be used in any system as long as the system includes the non-contact biometric sensor 3 and the camera 4.

As described above, the biological information acquisition device 5 according to the first embodiment includes the detection-value acquisition unit 11 that acquires a detection value from the non-contact biometric sensor 3, the vital measurement unit 12 that measures the vital signs of the target person TP using the detection value, the image-data acquisition unit 13 that acquires image data indicating an image captured by the camera 4, the image processing unit 14 that performs at least one of the state estimation process of estimating the state of the target person TP, the attribute estimation process of estimating the attribute of the target person TP, or the personal identification process of identifying the target person TP by performing image processing on a captured image including the target person TP, and the parameter setting unit 15 that sets parameters in measuring vital signs in accordance with the result of the image processing. This enables the adjustment of various parameters in vital sign measurement using the non-contact biometric sensor 3.

In addition, the parameters include the first parameter corresponding to the irradiation position of the measurement wave from the non-contact biometric sensor 3, and the parameter setting unit 15 sets the first parameter in accordance with at least one of the result of the state estimation process or the result of the personal identification process. As a result, the adjustment of the irradiation position can be achieved.

In addition, the state estimation process includes a process of estimating the heart position of the target person TP, the personal identification information corresponding to the target person TP is acquired by performing the personal identification process, and the parameter setting unit 15 sets the first parameter in accordance with at least one of the heart position or the personal identification information. As a result, the adjustment of the irradiation position can be achieved.

In addition, the parameters include the fourth parameter corresponding to the measurement range of the vital signs in the measurement, and the parameter setting unit 15 sets the fourth parameter in accordance with at least one of the result of the state estimation process, the result of the attribute estimation process, or the result of the personal identification process. As a result, the adjustment of the measurement range can be achieved.

In addition, the state estimation process includes a process of estimating the expression of the target person TP, the attribute estimation process includes at least one of a process of estimating the age of the target person TP or a process of estimating the gender of the target person TP, the personal identification information corresponding to the target person TP is acquired by performing the personal identification process, and the parameter setting unit 15 sets the fourth parameter in accordance with at least one of the expression, the age, the gender, or the personal identification information. As a result, the adjustment of the measurement range can be achieved.

Further, the parameters include the second parameter corresponding to a frame used for measurement, and the parameter setting unit 15 sets the second parameter in accordance with the result of the state estimation process. As a result, the adjustment of the measurement frame can be achieved.

In addition, the state estimation process includes at least one of a process of estimating the amount of body motion of the target person TP or a process of estimating the degree of mouth opening of the target person TP, and the parameter setting unit 15 sets the second parameter in accordance with at least one of the amount of body motion or the degree of mouth opening. As a result, the adjustment of the measurement frame can be achieved.

Furthermore, the parameters include the third parameter corresponding to the section width of the moving average process in the measurement, and the parameter setting unit 15 sets the third parameter in accordance with the result of the state estimation process. As a result, the adjustment of the moving average section width can be achieved.

In addition, the state estimation process includes at least one of the process of estimating the amount of body motion of the target person TP or the process of estimating the degree of mouth opening of the target person TP, and the parameter setting unit 15 sets the third parameter in accordance with at least one of the amount of body motion or the degree of mouth opening. As a result, the adjustment of the moving average section width can be achieved.

Furthermore, the biological information acquisition method according to the first embodiment includes step ST4 to cause the detection-value acquisition unit 11 to acquire a detection value from the non-contact biometric sensor 3, step ST5 to cause the vital measurement unit 12 to measure the vital signs of the target person TP using the detection value, step ST1 to cause the image-data acquisition unit 13 to acquire image data indicating an image captured by the camera 4, step ST2 to cause the image processing unit 14 to perform at least one of the state estimation process of estimating the state of the target person TP, the attribute estimation process of estimating the attribute of the target person TP, or the personal identification process of identifying the target person TP by performing image processing on the captured image including the target person TP, and step ST3 to cause the parameter setting unit 15 to set parameters in measuring vital signs in accordance with the result of the image processing. This enables the adjustment of various parameters in vital sign measurement using the non-contact biometric sensor 3.

Second Embodiment

Figure 10:
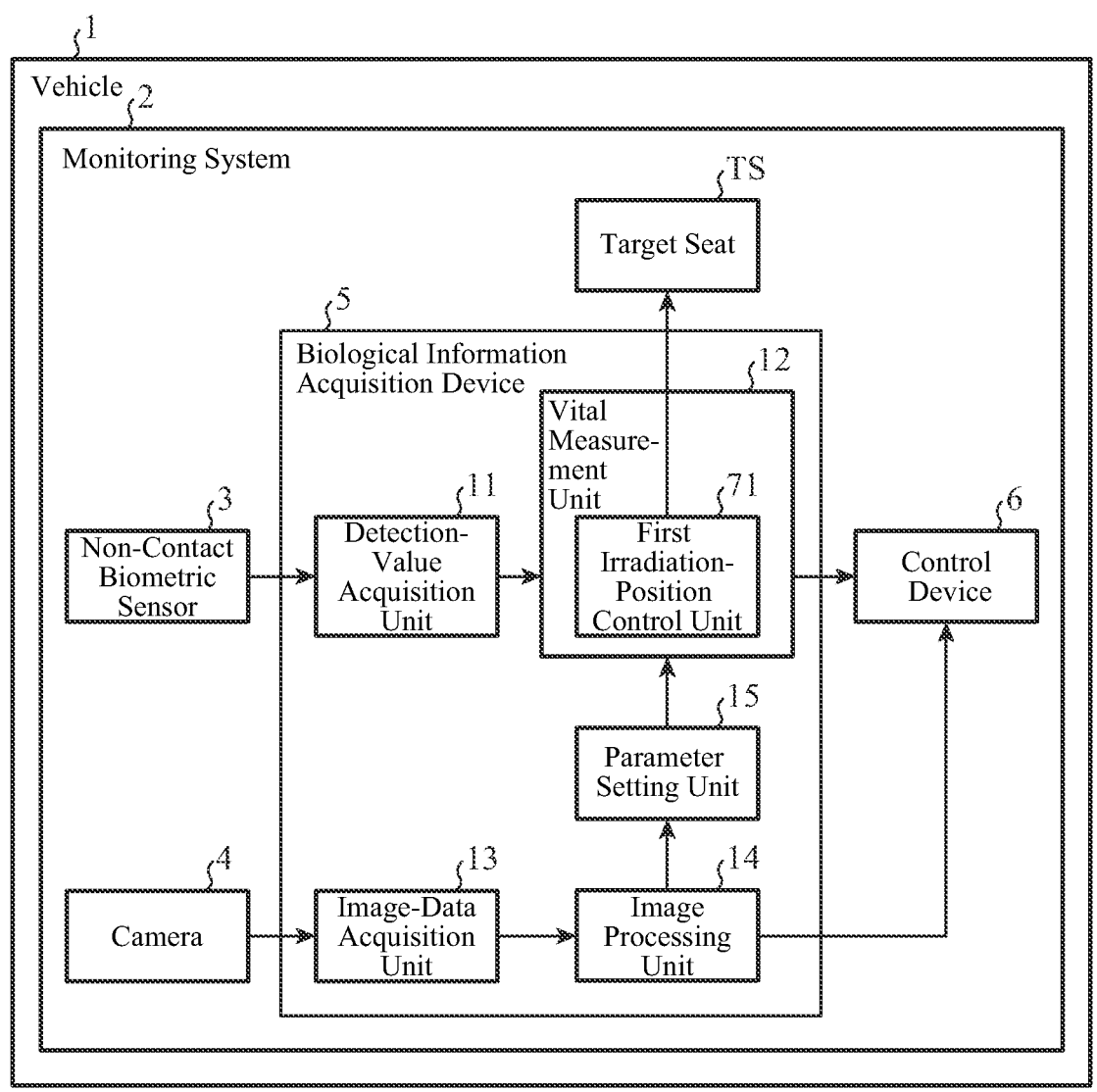
FIG. 10 is a block diagram illustrating a main part of a monitoring system including a biological information acquisition device according to a second embodiment.
Figure 11:
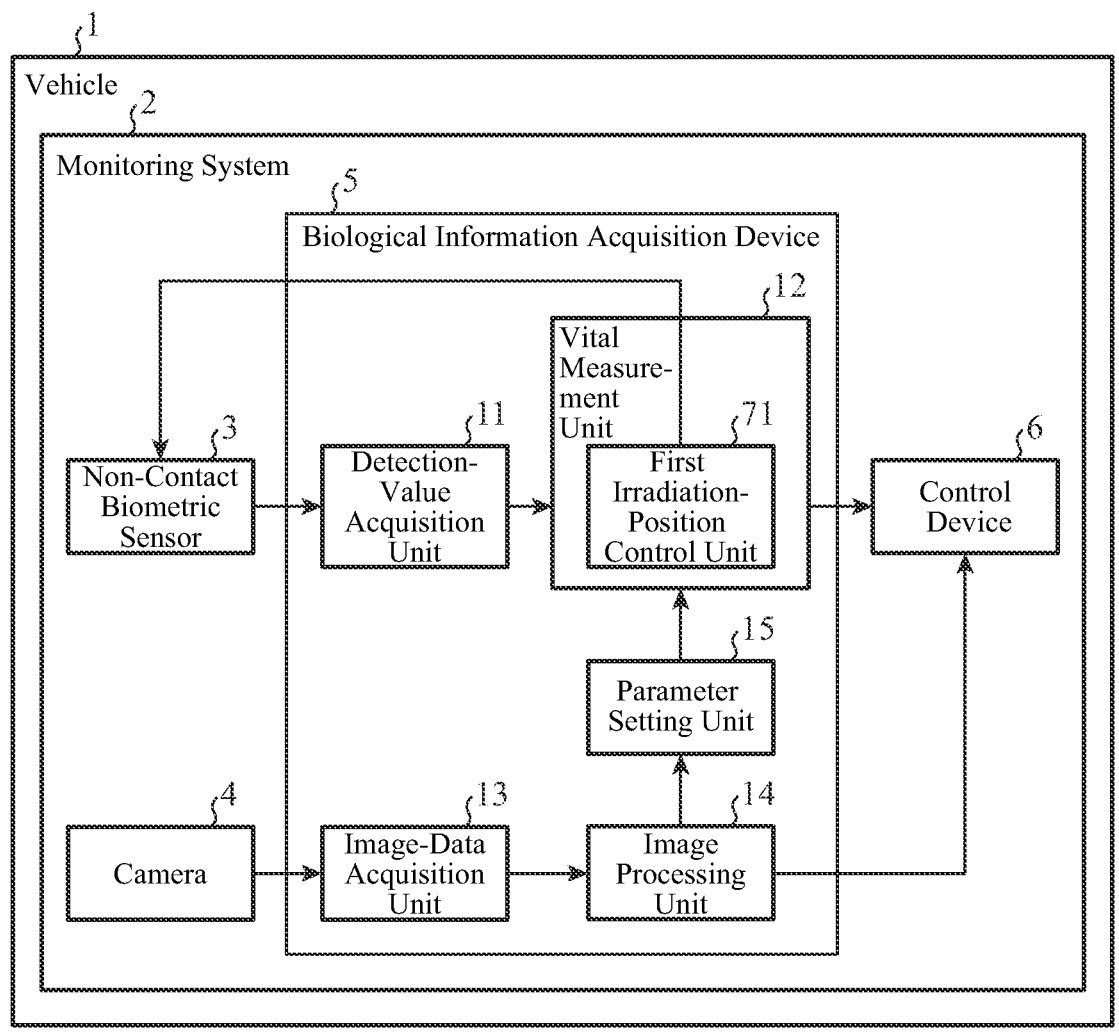
FIG. 11 is a block diagram illustrating a main part of a monitoring system including another biological information acquisition device according to the second embodiment.
Figure 12:
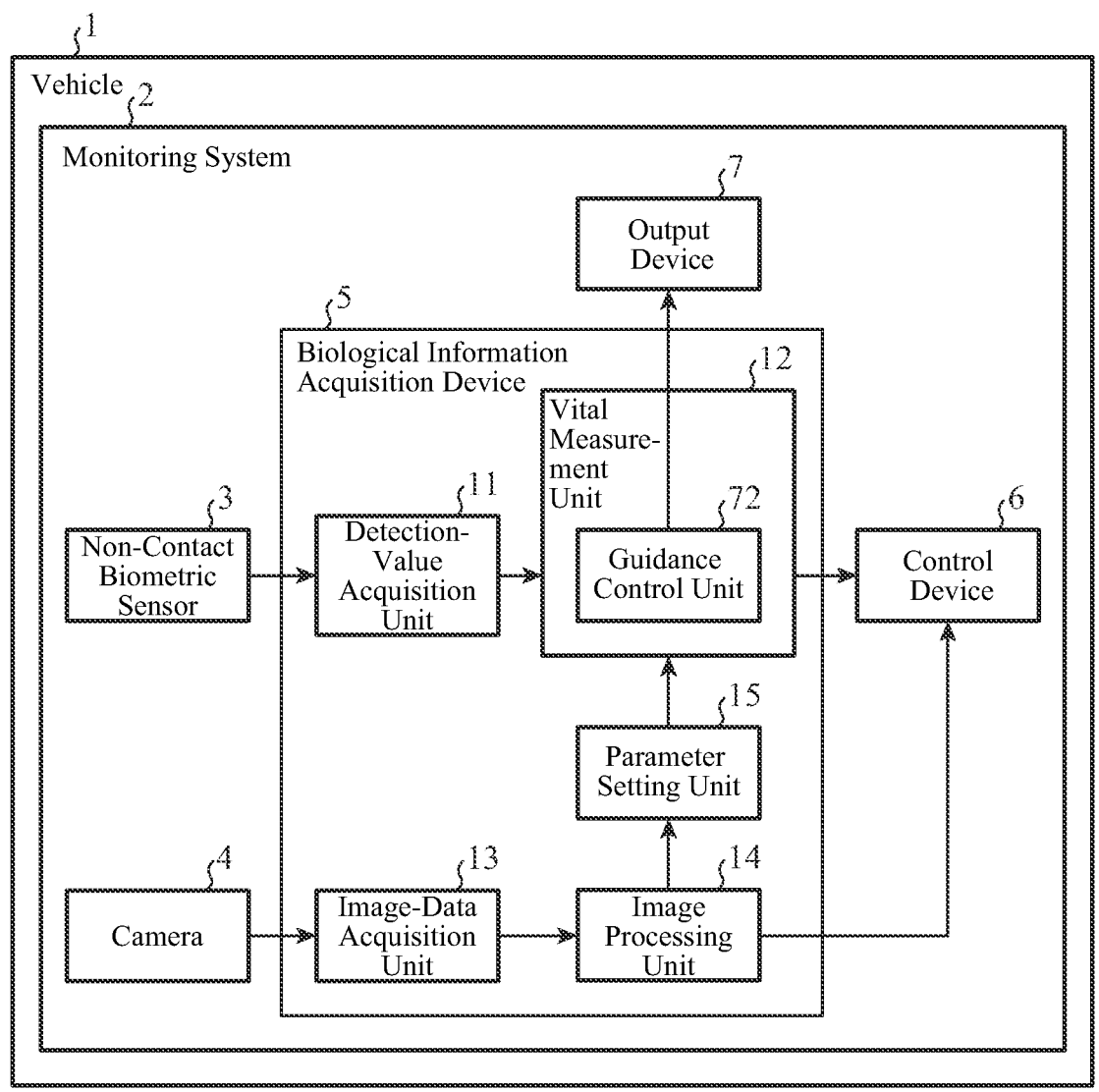
FIG. 12 is a block diagram illustrating a main part of a monitoring system including yet another biological information acquisition device according to the second embodiment.
Figure 13:
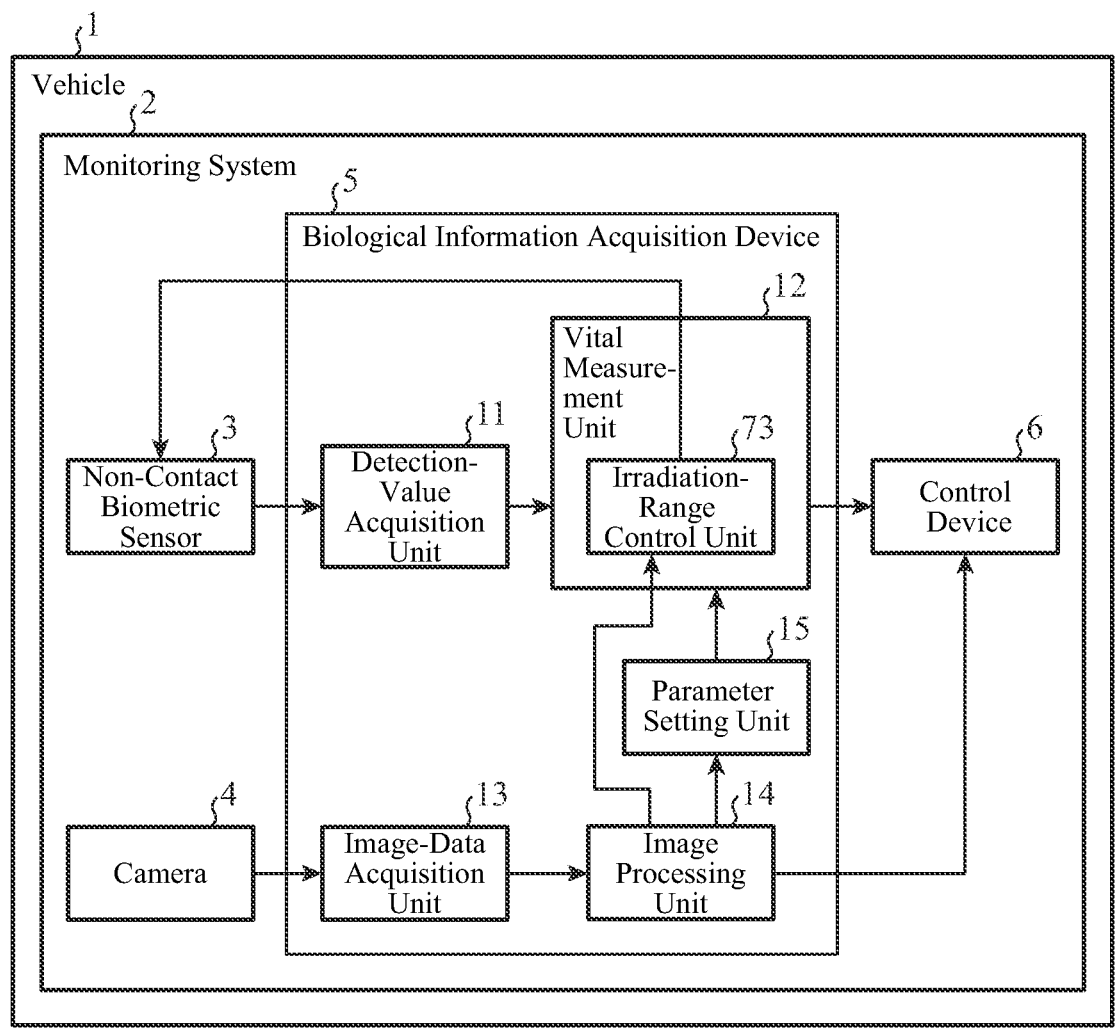
FIG. 13 is a block diagram illustrating a main part of a monitoring system including still another biological information acquisition device according to the second embodiment.
Figure 14:
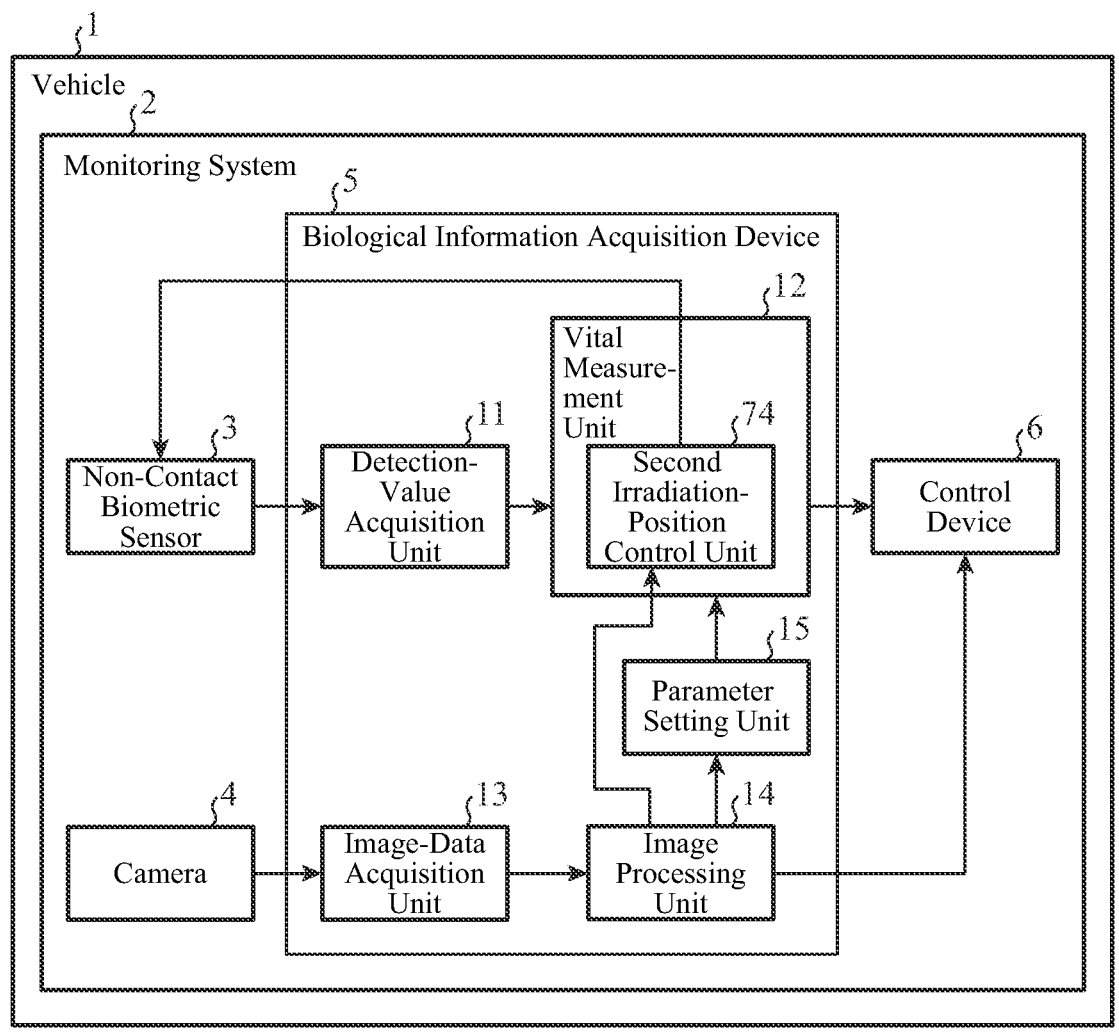
FIG. 14 is a block diagram illustrating a main part of a monitoring system including further biological information acquisition device according to the second embodiment.

FIG. 10 is a block diagram illustrating a main part of a monitoring system including a biological information acquisition device according to a second embodiment. FIG. 11 is a block diagram illustrating a main part of a monitoring system including another biological information acquisition device according to the second embodiment. FIG. 12 is a block diagram illustrating a main part of a monitoring system including yet another biological information acquisition device according to the second embodiment. FIG. 13 is a block diagram illustrating a main part of a monitoring system including still another biological information acquisition device according to the second embodiment. FIG. 14 is a block diagram illustrating a main part of a monitoring system including further biological information acquisition device according to the second embodiment.

The monitoring system including the biological information acquisition device according to the second embodiment will be described with reference to each of FIGS. 10 to 14. Note that, in each of FIGS. 10 to 14, the same reference numerals are given to blocks similar to those illustrated in FIG. 1, and description thereof will be omitted.

As illustrated in FIG. 10 or 11, the vital measurement unit 12 may include a first irradiation-position control unit 71. The first irradiation-position control unit 71 executes control (hereinafter, referred to as "irradiation position control") to align an irradiation position with a heart position on the basis of a first parameter set by the first parameter setting unit 51. Hereinafter, a specific example of the irradiation position control will be described.

First Specific Example of Irradiation Position Control (See FIG. 10)

The first irradiation-position control unit 71 executes control to operate the target seat TS depending on the difference between the current irradiation position and the heart position indicated by the first parameter. More specifically, the first irradiation-position control unit 71 executes control to operate at least one of the position of the target seat TS in a front-rear direction, the position of the target seat TS in the left-right direction, the position of the target seat TS in the vertical direction, the rotation angle of the target seat TS, or the reclining angle of the target seat TS. As a result, the irradiation position is adjusted to a position corresponding to the heart position. More specifically, the irradiation position is adjusted to substantially the same position as the heart position.

Second Specific Example of Irradiation Position Control (See FIG. 11)

The first irradiation-position control unit 71 executes control to mechanically rotate the non-contact biometric sensor 3 depending on the difference between the current irradiation position and the heart position indicated by the first parameter. As a result, the irradiation position is adjusted to a position corresponding to the heart position.

More specifically, the irradiation position is adjusted to substantially the same position as the heart position.

Third Specific Example of Irradiation Position Control (See FIG. 11)

The first irradiation-position control unit 71 performs a beamforming process on the non-contact biometric sensor 3 depending on the difference between the current irradiation position and the heart position indicated by the first parameter. As a result, the irradiation position is adjusted to a position corresponding to the heart position. More specifically, the irradiation position is adjusted to substantially the same position as the heart position.

Fourth Specific Example of Irradiation Position Control

The irradiation position control may be executed by combining the operation of the target seat TS and the rotation of the non-contact biometric sensor 3. Alternatively, the irradiation position control may be executed by combining the operation of the target seat TS and the beamforming process on the non-contact biometric sensor 3. Alternatively, the irradiation position control may be executed by combining the rotation of the non-contact biometric sensor 3 and the beamforming process on the non-contact biometric sensor 3. Alternatively, the irradiation position control may be executed by combining the operation of the target seat TS, the rotation of the non-contact biometric sensor 3, and the beamforming process on the non-contact biometric sensor 3.

Note that, in a case where the non-contact biometric sensor 3 is installed in the steering column of the vehicle 1, information indicating the attachment angle of the steering column in the vehicle 1 can be used for the irradiation position control.

As illustrated in FIG. 12, the vital measurement unit 12 may include a guidance control unit 72. The guidance control unit 72 executes control (hereinafter, referred to as "guidance control") to guide the heart of the target person TP to a measurement-wave irradiation position on the basis of the first parameter set by the first parameter setting unit 51. An output device 7 is used for the guidance control. The output device 7 includes at least one of a laser pointer, a speaker, a display, or an indicator. Hereinafter, a specific example of the guidance control will be described.

First Specific Example of Guidance Control

When the measurement-wave irradiation position is shifted from the heart position indicated by the first parameter, the guidance control unit 72 executes control to irradiate the measurement-wave irradiation position (that is, a suitable heart position) with a laser beam using a laser pointer.

The target person TP operates the target seat TS so as to align the chest of the target person TP (that is, the heart of the target person TP) with the measurement-wave irradiation position on the basis of the laser beam. That is, the target person TP manually performs an operation similar to the operation in the first specific example of the irradiation position control. In this manner, the heart of the target person TP is guided to the measurement-wave irradiation position.

Second Specific Example of Guidance Control

The guidance control unit 72 executes control to output a sound corresponding to the difference between the measurement-wave irradiation position and the heart position indicated by the first parameter using a speaker. Such a sound uses, for example, an intermittent sound whose intermittent interval changes depending on the amount of shift between the measurement-wave irradiation position and the heart position indicated by the first parameter. Alternatively, such a sound is, for example, a voice reading out a text indicating the direction of the irradiation position with respect to the heart position.

The target person TP operates the target seat TS so as to align the chest of the target person TP (that is, the heart of the target person TP) with the measurement-wave irradiation position on the basis of the sound. That is, the target person TP manually performs an operation similar to the operation in the first specific example of the irradiation position control. In this manner, the heart of the target person TP is guided to the measurement-wave irradiation position.

Third Specific Example of Guidance Control

The guidance control unit 72 executes control to display the presence or absence of the shift between the measurement-wave irradiation position and the heart position indicated by the first parameter using a display or an indicator.

The target person TP operates the target seat TS so as to align the chest of the target person TP (that is, the heart of the target person TP) with the measurement-wave irradiation position on the basis of the display. That is, the target person TP manually performs an operation similar to the operation in the first specific example of the irradiation position control. In this manner, the heart of the target person TP is guided to the measurement-wave irradiation position.

As illustrated in FIG. 13, the vital measurement unit 12 may include an irradiation-range control unit 73. The irradiation-range control unit 73 acquires information (hereinafter, referred to as "reliability information") indicating the reliability of the heart position estimated by the heart-position estimation unit 33 from the heart-position estimation unit 33. Alternatively, the irradiation-range control unit 73 calculates the reliability. Specifically, for example, the irradiation-range control unit 73 calculates the reliability on the basis of the signal intensity of a signal corresponding to vital signs measured by the vital measurement unit 12. The irradiation-range control unit 73 controls the range (hereinafter, sometimes referred to as "irradiation range") irradiated with a measurement wave by the non-contact biometric sensor 3 in accordance with the reliability indicated by the acquired reliability information or the calculated reliability.

Specifically, for example, in a case where the reliability is greater than or equal to a predetermined value (hereinafter, referred to as "reference value"), the irradiation-range control unit 73 sets a narrower range as the irradiation range. On the other hand, in a case where the reliability is less than the reference value, the irradiation-range control unit 73 sets a wider range as the irradiation range.

An error may occur in the estimation of the heart position by the heart-position estimation unit 33 depending on the orientation of the body of the target person TP or the position of the arm of the target person TP. When such an error occurs, the irradiation-range control unit 73 controls the irradiation range as described above, so that it is possible to avoid the case where the heart of the target person TP is not irradiated with the measurement wave.

As illustrated in FIG. 14, the vital measurement unit 12 may include a second irradiation-position control unit 74. The second irradiation-position control unit 74 acquires the reliability information from the heart-position estimation unit 33. Alternatively, the second irradiation-position control unit 74 calculates the reliability by a calculation method similar to the calculation method performed by the irradiation-range control unit 73. The second irradiation-position control unit 74 controls the measurement-wave irradiation position in accordance with the reliability indicated by the acquired reliability information or the calculated reliability.

Specifically, for example, in a case where the reliability is less than the reference value, the second irradiation-position control unit 74 sets the measurement-wave irradiation position to a predetermined initial position. In other words, the second irradiation-position control unit 74 resets the measurement-wave irradiation position.

Alternatively, for example, in a case where the reliability is less than the reference value, the second irradiation-position control unit 74 sets the measurement-wave irradiation position to the following position. That is, the second irradiation-position control unit 74 sets the measurement-wave irradiation position to a position similar to the last irradiation position set on the basis of the heart position corresponding to the reliability greater than or equal to the reference value.

An error may occur in the estimation of the heart position by the heart-position estimation unit 33 depending on the orientation of the body of the target person TP or the position of the arm of the target person TP. When such an error occurs, the second irradiation-position control unit 74 controls the irradiation position as described above, so that it is possible to avoid the case where the heart of the target person TP is not irradiated with the measurement wave.

As described above, in the biological information acquisition device 5 according to the second embodiment, the vital measurement unit 12 includes the first irradiation-position control unit 71 that executes the irradiation position control to align the irradiation position with the heart position on the basis of the first parameter. As a result, the irradiation position can be adjusted to a position suitable for measuring vital signs (particularly, a heart rate).

In addition, the vital measurement unit 12 includes the guidance control unit 72 that executes the guidance control to guide the heart of the target person TP to the irradiation position on the basis of the first parameter. As a result, the heart of the target person TP can be guided to a position suitable for measuring vital signs (in particular, a heart rate).

Furthermore, the vital measurement unit 12 includes the irradiation-range control unit 73 that controls the range irradiated with a measurement wave by the non-contact biometric sensor 3 in accordance with the reliability of the heart position. As a result, when an error occurs in the estimation of the heart position, it is possible to avoid the case where the heart of the target person TP is not irradiated with the measurement wave.

In addition, the vital measurement unit 12 includes the second irradiation-position control unit 74 that controls the irradiation position in accordance with the reliability of the heart position. As a result, when an error occurs in the estimation of the heart position, it is possible to avoid the case where the heart of the target person TP is not irradiated with the measurement wave.

Note that it is possible to freely combine the embodiments, modify any component of each embodiment, or omit any component of each embodiment within the scope of the present disclosure.

INDUSTRIAL APPLICABILITY

The biological information acquisition device according to the present disclosure can be used for, for example, a DMS or an OMS.

REFERENCE SIGNS LIST

1: vehicle, 2: monitoring system, 3: non-contact biometric sensor, 4: camera, 5: biological information acquisition device, 6: control device, 11: detection-value acquisition unit, 12: vital measurement unit, 13: image-data acquisition unit, 14: image processing unit, 15: parameter setting unit, 21: state estimation unit, 22: attribute estimation unit, 23: personal identification unit, 31: head-position estimation unit, 32: skeleton estimation unit, 33: heart-position estimation unit, 34: body-motion-amount estimation unit, 35: mouth-opening-degree estimation unit, 36: expression estimation unit, 41: age estimation unit, 42: gender estimation unit, 51: first parameter setting unit, 52: second parameter setting unit, 53: third parameter setting unit, 54: fourth parameter setting unit, 61: processor, 62: memory, 63: processing circuit, 71: first irradiation-position control unit, 72: guidance control unit, 73: irradiation-range control unit, 74: second irradiation-position control unit

The invention claimed is:

1. A biological information acquisition device comprising:
    processing circuitry configured to acquire a detection value from a non-contact biometric sensor;
    measure a vital sign of a target person using the detection value;
    acquire image data indicating an image captured by a camera;
    perform at least one of a state estimation process of estimating a state of the target person, an attribute estimation process of estimating an attribute of the target person, or a personal identification process of identifying the target person by performing image processing on the image captured including the target person; and
    set a parameter in measuring the vital sign in accordance with a result of the image processing,
    wherein the parameter includes a fourth parameter corresponding to a measurement range of the vital sign in the measurement,
    the processing circuitry sets the fourth parameter in accordance with at least one of a result of the state estimation process, a result of the attribute estimation process, or a result of the personal identification process,
    the state estimation process includes a process of estimating an expression of the target person,
    the attribute estimation process includes at least one of a process of estimating an age of the target person or a process of estimating a gender of the target person,
    personal identification information corresponding to the target person is acquired by performing the personal identification process, and
    the processing circuitry sets the fourth parameter in accordance with at least one of the expression, the age, the gender, or the personal identification information.

2. The biological information acquisition device according to claim 1, wherein
    the parameter includes a first parameter corresponding to an irradiation position of a measurement wave from the non-contact biometric sensor, and
    the processing circuitry sets the first parameter in accordance with at least one of a result of the state estimation process or a result of the personal identification process.

3. The biological information acquisition device according to claim 2, wherein
    the state estimation process includes a process of estimating a heart position of the target person,
    personal identification information corresponding to the target person is acquired by performing the personal identification process, and
    the processing circuitry sets the first parameter in accordance with at least one of the heart position or the personal identification information.

4. The biological information acquisition device according to claim 1, wherein
    the parameter includes the second parameter corresponding to a frame used for the measurement, and
    the processing circuitry sets the second parameter in accordance with a result of the state estimation process.

5. The biological information acquisition device according to claim 4, wherein
    the state estimation process includes at least one of a process of estimating an amount of body motion of the target person or a process of estimating a degree of mouth opening of the target person, and
    the processing circuitry sets the second parameter in accordance with at least one of the amount of body motion or the degree of mouth opening.

6. The biological information acquisition device according to claim 1, wherein
    the parameter includes the third parameter corresponding to a section width of a moving average process in the measurement, and
    the processing circuitry sets the third parameter in accordance with a result of the state estimation process.

7. The biological information acquisition device according to claim 6, wherein
    the state estimation process includes at least one of a process of estimating an amount of body motion of the target person or a process of estimating a degree of mouth opening of the target person, and
    the processing circuitry sets the third parameter in accordance with at least one of the amount of body motion or the degree of mouth opening.

8. The biological information acquisition device according to claim 1, wherein
    the non-contact biometric sensor and the camera are mounted on a vehicle, and
    the target person includes at least one of a driver of the vehicle or a passenger of the vehicle.

9. The biological information acquisition device according to claim 1, wherein the non-contact biometric sensor is a radio-wave non-contact biometric sensor.

10. The biological information acquisition device according to claim 1, wherein the vital sign includes at least one of a heart rate or a respiratory rate.

11. The biological information acquisition device according to claim 3, wherein the processing circuitry is further configured to execute irradiation position control to align the irradiation position with the heart position on a basis of the first parameter.

12. The biological information acquisition device according to claim 11, wherein the irradiation position control is executed by operating a target seat when the target person is seated on the target seat.

13. The biological information acquisition device according to claim 11, wherein the irradiation position control is executed by rotating the non-contact biometric sensor.

14. The biological information acquisition device according to claim 11, wherein the irradiation position control is executed by performing a beamforming process on the non-contact biometric sensor.

15. The biological information acquisition device according to claim 3, wherein the processing circuitry is further configured to execute guidance control to guide a heart of the target person to the irradiation position on a basis of the first parameter.

16. The biological information acquisition device according to claim 15, wherein the guidance control uses a laser beam for guidance, a sound for guidance, or a display for guidance.

17. The biological information acquisition device according to claim 3, wherein the processing circuitry is further configured to control an irradiation range of the measurement wave from the non-contact biometric sensor in accordance with reliability of the heart position.

18. The biological information acquisition device according to claim 3, wherein the processing circuitry is further configured to control the irradiation position in accordance with reliability of the heart position.

19. A biological information acquisition method comprising:
   acquiring a detection value from a non-contact biometric sensor;
   measuring a vital sign of a target person using the detection value;
   acquiring image data indicating an image captured by a camera;
   performing at least one of a state estimation process of estimating a state of the target person, an attribute estimation process of estimating an attribute of the target person, or a personal identification process of identifying the target person by performing image processing on the image captured including the target person; and
   setting a parameter in measuring the vital sign in accordance with a result of the image processing,
   wherein the parameter includes a fourth parameter corresponding to a measurement range of the vital sign in the measurement, and the method further comprises setting the fourth parameter in accordance with at least one of a result of the state estimation process, a result of the attribute estimation process, or a result of the personal identification process, and
   wherein the state estimation process includes a process of estimating an expression of the target person,
   the attribute estimation process includes at least one of a process of estimating an age of the target person or a process of estimating a gender of the target person,
   personal identification information corresponding to the target person is acquired by performing the personal identification process, and
   the method comprises setting the fourth parameter in accordance with at least one of the expression, the age, the gender, or the personal identification information.

* * * * *